(12) United States Patent
Bond et al.

(10) Patent No.: US 6,787,042 B2
(45) Date of Patent: Sep. 7, 2004

(54) AUTOMATED RADIONUCLIDE SEPARATION SYSTEM AND METHOD

(75) Inventors: Andrew H. Bond, Arlington Heights, IL (US); John J. Hines, Newark, IL (US); John E. Young, Woodridge, IL (US); E. Philip Horwitz, Naperville, IL (US)

(73) Assignee: PG Research Foundation, Darien, IL (US)

( * ) Notice: Subject to any disclaimer, the term of this patent is extended or adjusted under 35 U.S.C. 154(b) by 78 days.

(21) Appl. No.: 10/177,828

(22) Filed: Jun. 21, 2002

(65) Prior Publication Data

US 2003/0127395 A1 Jul. 10, 2003

Related U.S. Application Data

(60) Provisional application No. 60/300,141, filed on Jun. 22, 2001.

(51) Int. Cl.[7] .................................................. C02F 1/42
(52) U.S. Cl. ...................... 210/681; 210/682; 210/143; 210/278; 423/2; 423/249
(58) Field of Search ................................ 210/681, 682, 210/143, 278; 423/2, 3, 6, 7, 11, 249; 250/432 PD

(56) References Cited

U.S. PATENT DOCUMENTS

| | | | | |
|---|---|---|---|---|
| 3,774,036 A | * | 11/1973 | Gerhart | 252/645 |
| 3,989,624 A | * | 11/1976 | Wachsmuth | 210/677 |
| 5,854,968 A | | 12/1998 | Horwitz et al. | |
| 6,126,909 A | | 10/2000 | Rotmensch et al. | |
| 6,153,154 A | | 11/2000 | Egorov et al. | |

OTHER PUBLICATIONS

Whitlock, Ind. Eng. Chem. Res. (2000), 39:3135–3139.
Hassfjell et al., Chem. Rev. (2001) 101:2019–2036.
Imam, J. Radiation Oncology Biol. Phys. (2001) 51:271–278.
McDevitt et al., Science (2001) 294:1537–1540.
Choppin et al., *J. Nuclear Chemistry: Theory and Applications*; Pergamon Press: Oxford, 1980.
Gansow et al., In *Radionuclide Generators: New Systems for Nuclear Medicine Applications*.
Knapp et al. Eds., *Radionuclide Generators: New Systems for Nuclear Medicine Applications* American Chemical Society: Washington, DC (1984) vol. 241.
Dietz et al., Appl. Radiat. Isot. (1992) 43:1093–1101.
Mirzadeh et al., J. Radioanal. Nucl. Chem (1996) 203:471–488.
Lambrecht et al., Radiochim. Acta (1997) 77:103–123.
Wu et al., Radiochim. Acta (1997) 79:141–144.

* cited by examiner

*Primary Examiner*—Robert A. Hopkins
(74) *Attorney, Agent, or Firm*—Welsh & Katz, Ltd.

(57) ABSTRACT

A gas-free system for separating a solution of substantially impurity-free daughter products from an associated parent load solution includes a pump, a plurality of multi-port valves, separation medium and a processor. An uncoiled conduit extends between a third port of a second multi-port valve and a first multi-port valve. A processor is operably coupled to a pump, and the plurality of multi-port valves. A method for separating a solution of substantially impurity-free daughter product from an associated parent load solution is also disclosed.

31 Claims, 13 Drawing Sheets

AUTOMATED RADIONUCLIDE SEPARATION SYSTEM AND METHOD

CROSS-REFERENCE TO RELATED APPLICATIONS

This application claims the benefit of U.S. Provisional Application Ser. No. 60/300,141 filed Jun. 22, 2001.

FIELD OF THE INVENTION

The present invention relates to a system and method for the separation of substantially impurity-free radionuclides. More particularly, the present invention relates to a system and method for the separation of a solution of a substantially impurity-free solution containing daughter radionuclides from a solution containing the daughter radionuclide and parent radionuclides.

BACKGROUND

Radioactive materials have a variety of uses including, for example, medical applications in radiodiagnostics and radiotherapeutics. For example, alpha and beta emitting radionuclides have been found to be effective in the treatment and eradication of microscopic disease. Examples of such radionuclides, include, for example, yttrium-90, bismuth-212 and -213, and rhenium-188. The efficacy of such treatments is believed to be a result of the densely ionizing radiation that is emitted during decay.

It has been shown that lead-212 (Pb-212), astatine-211 (At-211), bismuth-212 (Bi-212), bismuth-213 (Bi-213), and yttrium-90 (Y-90) are effective in the treatment and eradication of microscopic carcinoma. In some cases, known methods for producing such alpha or beta particle emitting nuclides are limited in that they generally require the use of particle accelerators or nuclear reactors for their production. Moreover, the radionuclides are often contaminated with impurities, both chemical and radiochemical, that are difficult to filter out or otherwise remove from the desired nuclide.

It has also been found that such nuclides contaminated with impurities do not have the desired property of even distribution to the affected area after administration. Further, the desired radionuclide material and the parent materials emit harmful radiation, exposing the user to great danger. Convenient methods for the separation of Bi-212 and Bi-213 from parental streams have recently been patented. See, Horwitz et al. U.S. Pat. No. 5,854,968 and Rotmensch et al. U.S. Pat. No. 6,126,909, the disclosures of which are incorporated herein by reference.

Moreover, many alpha and beta emitting isotopes have short half-lives. For example, Bi-213 has a half-life of about 45.6 minutes and ultimately decays to stable Bi-209. Therefore, it would be most desirable to produce the desired isotope at a location remote from a particle accelerator or other source, and as physically close to the clinical environment as possible.

Radionuclides can also be used for body imaging or radiodiagnostic purposes to determine the presence of a harmful disease, such as a carcinoma, in an early stage so the disease can be treated early, thus increasing the chance of successful treatment. The radionuclides technetium-99m, thallium-201, fluorine-18, or indium-111, for example, can be used for radiodiagnostic purposes.

Some of these desired radionuclides are "grown" from parent radionuclides. That is, the parent radionuclide is stored for a predetermined period of time to permit the parent to produce the desired daughter radionuclide through radioactive decay. The daughter product must then be separated from the parent as well as any other contaminants that may be present. These processes are typically carried out in solution.

Of importance in the preparation of these, as well as other radionuclides, is the effort to reduce the radiation exposure to the operator, as well as others that are in the general vicinity of the "growing" and separation processes. Although the daughter products may be alpha-emitting particles, and as such are less problematic to shield, the parent radionuclide, as well as granddaughter products and other possibly present radionuclides can be gamma- and beta-emitters. As such, these "growing" and separation systems should be well shielded and contained.

The principle of minimizing radiation exposure to all persons is well-known and accepted as the principle of "As Low As Reasonably Achievable" or ALARA. ALARA principles and objectives are adopted in the handling and use of all radioactive materials.

U.S. Pat. No. 6,153,154 ('154 patent') discloses a method of separating Bi-213 from an Ac-225 (actinium-225) parent solution. However, the method disclosed has many disadvantages including the usage of gas during separation, the possible loss of precious parent solution, and inadequate purification of the daughter, among other disadvantages.

Accordingly, there is a need for a method and system for the production of substantially impurity-free radionuclides in a localized, contained manner, and for a method and system that does not have some or all of the disadvantages the method of the 154 patent has. Desirably, such an apparatus is sufficiently portable so that it can be transported to a patient for administration and treatment without special facilities. Further, such a system and method minimizes an operator's exposure to harmful radiation.

Chemical purity is vital to a safe and efficient medical procedure because the radionuclide is generally conjugated to a biolocalization agent prior to use. This conjugation reaction relies on the principles of coordination chemistry wherein a radionuclide is chelated to a ligand that is covalently attached to the biolocalization agent. In a chemically impure sample, the presence of ionic impurities can interfere with this conjugation reaction. If sufficient $^{99m}$Tc, for example, is not coupled to a given biolocalization agent, poorly defined images are obtained due to insufficient photon density localized at the target site and/or from an elevated in vivo background due to aspecific distribution in the blood pool or surrounding tissues.

Regulation of radionuclidic purity stems from the hazards associated with the introduction of long-lived or high energy radioactive impurities into a patient, especially if the biolocalization and body clearance characteristics of the radioactive impurities are unknown. Radionuclidic impurities pose the greatest threat to patient welfare, and such impurities are the primary focus of clinical quality control measures that attempt to prevent the administration of harmful and potentially fatal doses of radiation to the patient.

The use of radiation in disease treatment has long been practiced, with the mainstay external beam radiation therapy now giving way to more targeted delivery mechanisms such as radioimmunotherapy (RIT), which employs radionuclide conjugation to peptides, proteins, or antibodies that selectively concentrate at the disease site whereby radioactive decay imparts cytotoxic effects. Radioimmunotherapy represents the most selective means of delivering a cytotoxic dose of radiation to diseased cells while sparing healthy tissue. (See, Whitlock, Ind. Eng. Chem. Res. (2000), 39:3135–3139; Hassfjell et al., Chem. Rev. (2001) 101:2019–2036; Imam, J. Radiation Oncology Biol. Phys. (2001) 51:271–278; and McDevitt et al., Science (2001) 294:1537–1540.)

Candidate radionuclides for RIT typically have radioactive half-lives in the range of 30 minutes to several days, coordination chemistry that permits attachment to biolocalization agents, and a high linear energy transfer (LET). The LET is defined as the energy deposited in matter per unit pathlength of a charged particle, (see, Choppin et al., *J. Nuclear Chemistry: Theory and Applications*; Pergamon Press: Oxford, 1980) and the LET of alpha particles is substantially greater than beta particles. By example, alpha particles having a mean energy in the 5–9 MeV range typically expend their energy within about 50–90 $\mu$m in tissue, which corresponds to several cell diameters. The lower LET beta$^-$ particles having energies of about 0.5–2.5 MeV may travel up to 10,000 $\mu$m in tissue, and the low LET of these beta$^-$ emissions requires as many as 100,000 decays at the cell surface to afford a 99.99% cell-kill probability. For a single alpha particle at the cellular surface, however, the considerably higher LET provides a 20–40% probability of inducing cell death as the lone alpha particle traverses the nucleus. (See, Hassfjell et al., Chem. Rev. (2001) 101:2019–2036.)

Unfortunately, the LET that makes alpha and beta$^-$ emitting nuclides potent cytotoxic agents for cancer therapy also introduces many unique challenges into the production and purification of these radionuclides for use in medical applications. Foremost among these challenges is the radiolytic degradation of the support material that occurs when the conventional generator methodology is used with high LET radionuclides. (See, Hassfjell et al., Chem. Rev. (2001) 101:2019–2036; Gansow et al., In *Radionuclide Generators: New Systems for Nuclear Medicine Applications*; Knapp et al. Eds., American Chemical Society: Washington, D.C. (1984) pp 215–227; Knapp, et al. Eds., *Radionuclide Generators: New Systems for Nuclear Medicine Applications* American Chemical Society: Washington, D.C. (1984) Vol. 241; Dietz et al., Appl. Radiat. Isot. (1992) 43:1093–1101; Mirzadeh et al., J. Radioanal. Nucl. Chem. (1996) 203:471–488; Lambrecht et al., Radiochim. Acta (1997) 77:103–123; and Wu et al., Radiochim. Acta (1997) 79:141–144.)

Radiolytic degradation of the generator support material can result in: (a) diminished chemical purity (e.g., radiolysis products from the support matrix can contaminate the daughter solution); (b) compromised radionuclidic purity (e.g., the support material can release parent radionuclides to the eluate: termed "breakthrough"); (c) diminished yields of daughter radionuclides (e.g., alpha-recoil can force the parent radionuclides into stagnant regions of the support making their decay products less accessible to the stripping eluent); (d) decreases in column flow rates (e.g., fragmentation of the support matrix creates particulates that increase the pressure drop across the column); and (e) erratic performance (e.g., variability in product purity, nonreproducible yields, fluctuating flow rates, etc.). In order to minimize the adverse effects of radiolytic degradation on the chemical and radionuclidic purity of the product, the separation columns may be used a single time so that radiolytic degradation products do not accumulate and interfere with subsequent purification procedures. However, certain applications may allow for multiple uses. Thus, a convenient means of inserting the separation columns into the device and removing them after use is desirable.

BRIEF DESCRIPTION OF THE FIGURES

The benefits and advantages of the present invention will become more readily apparent to those of ordinary skill in the relevant art after reviewing the following detailed description and accompanying drawings, wherein.

DETAILED DESCRIPTION

Figure 1:
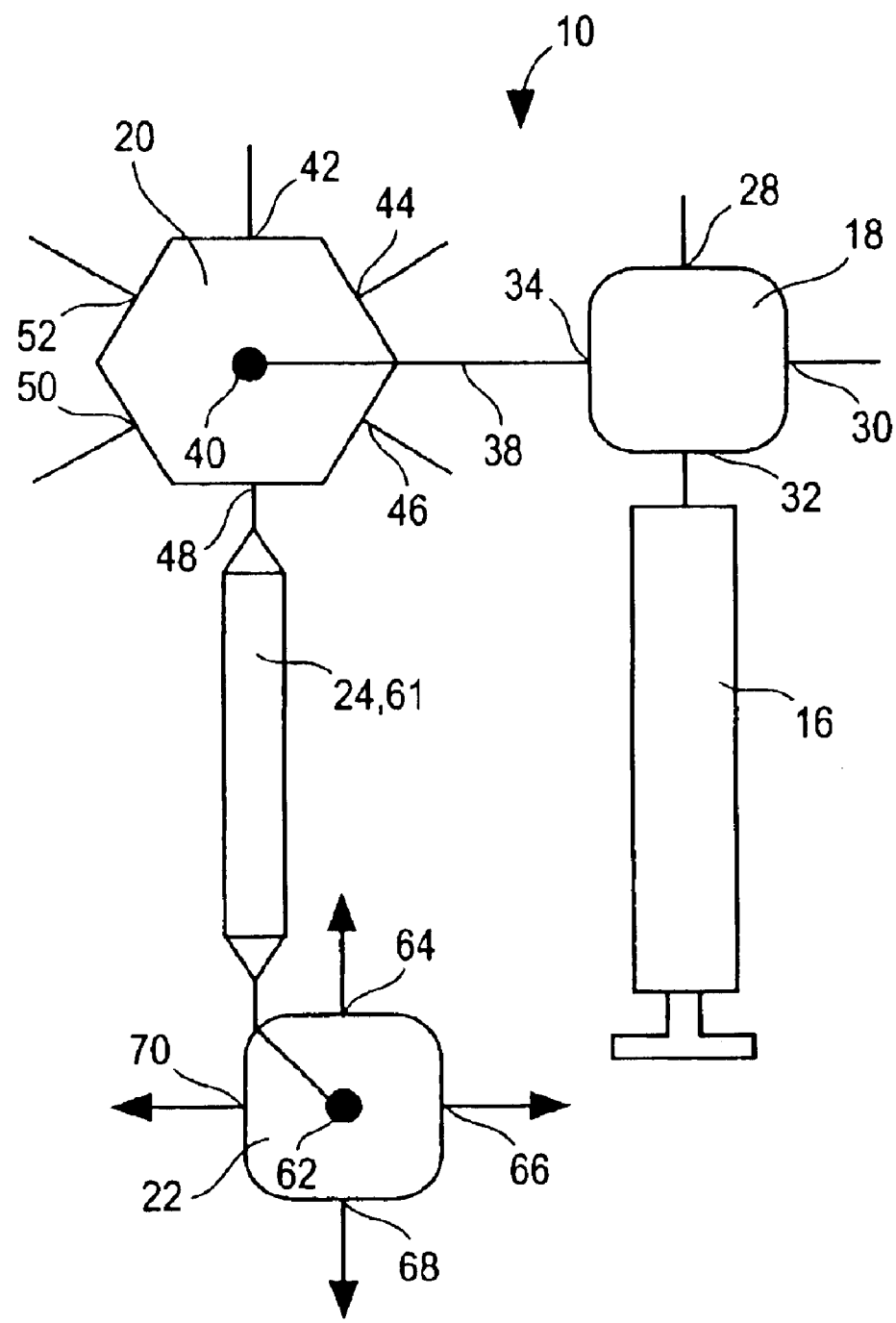
FIG. 1 illustrates a portion of one embodiment of an automated radionuclide separation system pursuant to the principles of the present invention, the system incorporating a separator, first, second, and third multi-port valves, and a pump.

Although the present invention is susceptible of embodiment in various forms, there is shown in the drawings and will hereinafter be described a specific embodiment with the understanding that the present disclosure is to be considered an exemplification of the invention and is not intended to limit the invention to the specific embodiment illustrated.

The present system and method relates to separation of a solution of a substantially impurity-free solution containing daughter radionuclides from a solution containing the daughter radionuclide and parent radionuclides. Decontaminations of about 1000 to about 1,000,000 or more can be achieved using a contemplated system and method.

Thus, one aspect of the system and method contemplates a gas-free system for separating a solution of substantially impurity-free daughter product such as a nuclide from an associated parent load solution. The system comprises a pump; a first multi-port valve having at least two ports, of which a first port is in flow communication with the pump; and a second multi-port valve that includes at least four ports. A first port of the second multi-port valve is in flow communication with the associated parent load solution, a second port of the second multi-port valve is in flow communication with an associated strip solution, a third port of the second multi-port valve is in flow communication with the first multi-port valve, and a fourth port. A separator is in flow communication with the fourth port of the second multi-port valve. A third multi-port valve including at least two ports is also present. That third multi-port valve has a first port that is in flow communication with the separator opposite the fourth port of the second multi-port valve, and a second port that is in flow communication with an associated product vessel. An uncoiled conduit extends between a third port of the second multi-port valve and the first multi-port valve. A processor operatively coupled to the pump, first multi-port valve, the second multi-port valve, and the third multi-port valve is used to control those components, and is preferably a mini-processor, capable of executing instructions.

A gas- and air-less method for separating a daughter radionuclide from a solution containing a parent radionuclide to form a solution of substantially impurity-free daughter radionuclide is also contemplated. In accordance with that method, a solution containing a parent radionuclide is transferred to a growth vessel. The parent radionuclide is maintained for a predetermined time, as by waiting, for decay of the parent to form a parent-daughter solution containing a desired daughter radionuclide. The parent-daughter solution is contacted with a separation medium having a high affinity for the daughter radionuclide and a low affinity for the parent radionuclide to form daughter-laden separation medium and a daughter-depleted parent-daughter solution. The daughter-depleted parent daughter solution is separated from the separation medium; and the desired daughter radionuclide is stripped from the daughter-laden separation medium to form a solution of substantially impurity-free daughter radionuclide.

One embodiment relates to an automated system 10, 200, 300 and method for separating a desired daughter radionuclide product 12 from a parent material 14. Specifically, the present invention is directed to an air-free or other gas-free system 10, 200, 300 and method for separating a solution containing substantially impurity-free daughter product 12 from a solution containing a parent radionuclide 14 and any intermediate radionuclides. An exemplary system includes, as will be described in detail below, a pump 16, a plurality of multi-port valves 18, 20, 22, a separator 24, 61 and preferably a processor 26 for controlling operation of the system 10.

The system 10, 200, 300 and method can be used to separate a variety of radionuclide daughter products from their parent radionuclides. For example, the invention can be used to separate yttrium-90 from strontium-90, bismuth-212 from lead-212, bismuth-213 from actinium-225, or rhenium-188 from tungsten-188, to provide daughter products that can be used for radiotherapy. The invention can also be used to purify technetium-99m, thallium-201, fluorine-18, or indium-111, which are daughter products that can be used for diagnostic imaging. The system and method are automated and the system may be within shielding to reduce user exposure according to ALARA principles.

Operation may be in one of two modes, a conventional radionuclide generator or conventional cow mode and a multicolumn selectivity inversion generator or reverse cow mode. In the conventional cow mode, a parent material 14 is loaded onto a separator 61, the parent product 14 is captured on the separator 61 and the desired daughter product 12 passes through the separator 61. In the reverse cow mode, the parent product 14 is not loaded onto the separator 24, while the desired daughter product 12 is captured on the separator 24. The parent solution 14 passes through the separator 24. Subsequently, the desired daughter product 12 is stripped from the separator 24.

Referring now to FIG. 1, there is shown a first embodiment of an automated radionuclide separation system 10 embodying the principles of the present invention. The system includes a drive 16, such as a pump 16, which can be a syringe pump 16, in flow communication with a first multi-port valve 18. The pump 16 can be powered by a motor (not shown), and provide motive force to move solutions through the system 10. Preferably the pump 16 is a high speed syringe pump 16, such as the model MBP2000 pump from Advanced Liquid Handling in Milwaukee, Wis. A 5 or 10 mL syringe size can be used. In other embodiments, a peristaltic pump may be used.

The first multi-port valve 18 is used to direct solution from the pump 16. The first valve 18 includes at least three ports 34, 30, 32. Although other types of valves can be used, the first multi-port valve shown in FIG. 1 is a selection valve having four ports 28, 30, 32, 34. Adjacent ports can be in communication with one another by way of an interior V-shaped plug (not shown). For example, a third port 32 can be in communication with a second port 30 or a fourth port 34, but not a first port 28.

In the illustrated embodiment, the third port 32 is in flow communication with the pump 16 and the second port 30 is in flow communication with a wash solution 36 (discussed below). The fourth port 34 is in flow communication with an uncoiled conduit 38 or tube 38 that is in flow communication with a second multi-port valve 20.

The second multi-port valve 20 has at least seven ports 40, 42, 44, 46, 48, 50, 52. Although other types of valves can be used, the second multi-port valve 20 shown in FIG. 1 is a six port distribution valve 20 having six side ports 42, 44, 46, 48, 50, 52 and one common port 40 (seven total ports). In the second valve 20 shown in FIG. 1, the common port 40 can be selectively in flow communication with any of the side ports 42, 44, 46, 48, 50, 52, but the side ports 42, 44, 46, 48, 50, 52 are not in flow communication with one another. The uncoiled tube 38 is in flow communication with the common port 40.

Figure 2:
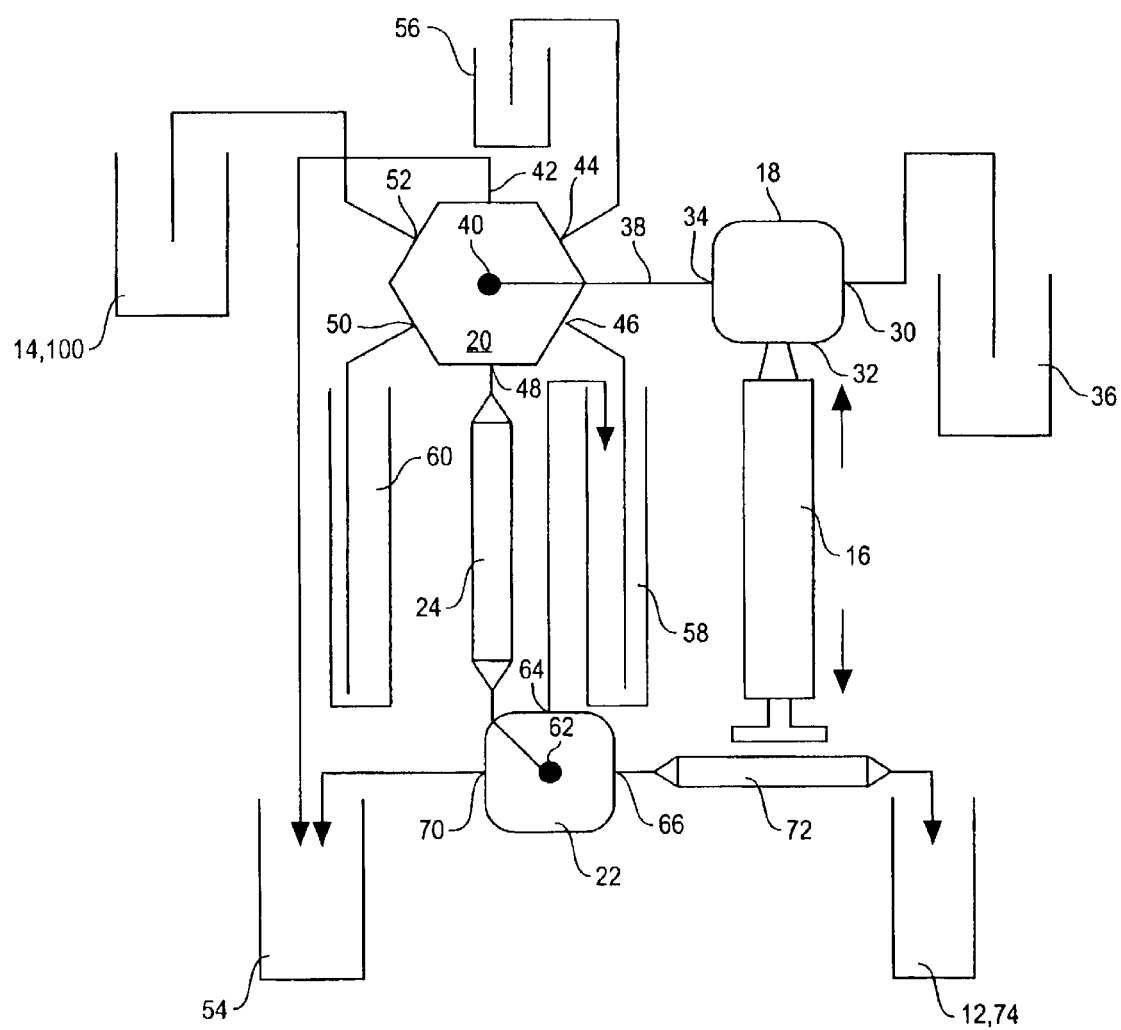
FIG. 2 shows a schematic illustration of the embodiment of the system of FIG. 1 that is configured to carry out a reverse cow (also referred to as a multicolumn selectivity inversion generator) method of separating a desired daughter product from a parent load solution, and further shows, by way of arrows, the direction of pump movement.

The side ports 42, 44, 46, 48, 50, 52 can be in flow communication with different solutions and vessels, such as containers, depending on the particular process that is to be carried out. For example, as shown in FIG. 2, in reverse cow mode, the first port 42 is in flow communication with a waste vessel 54, the second port 44 is in flow communication with a strip solution 56 (discussed below), the third port 46 is in flow communication with a temporary storage vessel 58, the fourth port 48 is in flow communication with a separator 24 (discussed below), the fifth port 50 is in flow communication with a growth vessel 60, and the sixth port 52 is in flow communication with a parent load solution 14 (discussed below).

As will be described in greater detail below, daughter activity forms from parent activity in the growth vessel 60. After separation, a solution containing substantially parent radionuclide (with the daughter radionuclide removed by the separator) is stored in the temporary storage vessel 58. During operation, a solution containing residual parent radionuclide and wash solution is also stored in the temporary storage vessel 58. Used wash solution is generally directed to the waste vessel 54.

Figure 3:
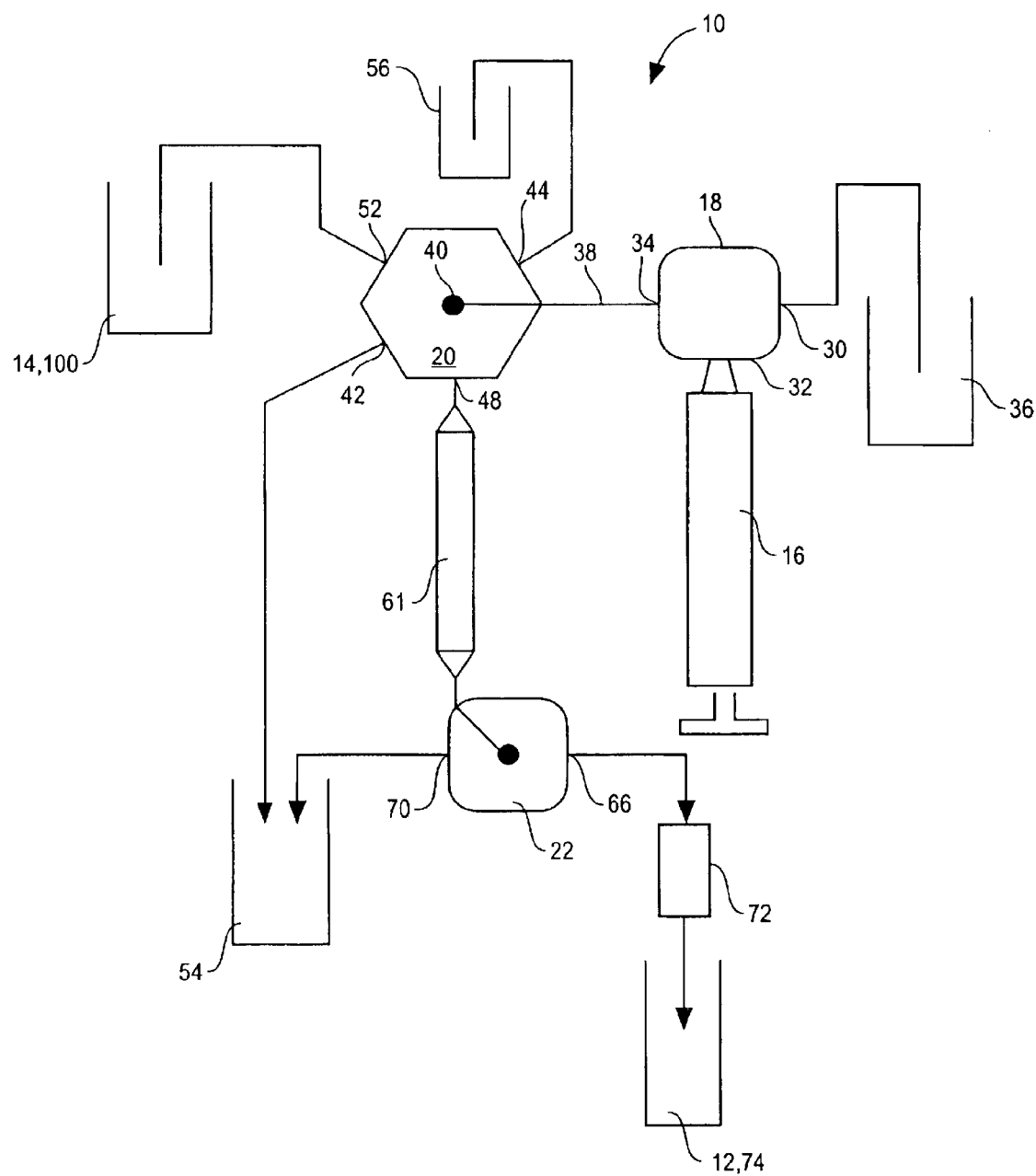
FIG. 3 is a schematic illustration of the embodiment of the system of FIG. 1 that is configured to carry out a conventional cow method of separating a desired daughter product from a parent load solution.

In conventional cow mode, as illustrated in FIG. 3, the first port 42 (shown in the position of the fifth port 50 of FIGS. 1–2) is in flow communication with the waste vessel 54, the second port 44 is in flow communication with a strip solution 56 (described below), the fourth port 48 is in flow communication with a separator 61 (discussed below), and the sixth port 52 is in flow communication with a parent load solution 14 (discussed below). As described in greater detail below, because only four side ports 42, 44, 48, 52 are in use when the first embodiment of the system 10 is in conventional cow mode, the second multi-port valve 20 need only be a distribution valve having four side ports and a common port. However, preferably, the system is configured to permit both conventional and reverse cow modes to be carried on a common system. Thus, the second multi-port valve is desirably a six port distribution valve as described above.

As shown in FIG. 1, the separator 24, 61 is in flow communication with the second multi-port valve 20 and a third multi-port valve 22. The separator 24 contains a separation medium that is used to separate the desired daughter radionuclide activity from parent radionuclide.

The third multi-port valve 22 has at least four ports 62, 64, 66, 68. Although other types of valves can be used, the third multi-port valve 22 shown in FIG. 1 is a four port distribution valve having four side ports 64, 66, 68, 70 and a common port 62 (five total ports). The common port 62 is selectively in flow communication with any of the side ports 64, 66, 68, 70, but the side ports 64, 66, 68, 70 are not in flow communication with one another. Preferably, the separator 24, 61 is in flow communication with the common port 62.

The side ports 64, 66, 68, 70 are in flow communication with different solutions and containers depending on which particular process; for example the conventional or reverse cow mode, is to be carried out. For example, as shown in FIG. 2, in reverse cow mode the first port 64 is in flow communication with the temporary storage vessel 58, the second port 66 is in flow communication with a guard separator 72 (discussed below), which is in flow communication with a product vessel 74, and the third port 70 is in flow communication with the waste vessel 54. As described below, the guard separator 72 is used to further separate the desired parent radionuclide from the daughter solution. The guard separator 72 may also be referred to as a guard column.

In conventional cow mode, as shown in FIG. 3, the second port 66 of multi-port valve 22 is in flow communication with the guard separator 72 (described below), which is in flow communication with the product vessel 74, and the third port 70 is in flow communication with the waste vessel 54. As shown in FIG. 3, because only two side ports 66, 70 are in use when in conventional cow mode, the third multi-port valve 22 need only be a distribution valve having two side ports and a common port. However, preferably, the first embodiment is configured for both conventional and reverse cow modes. Thus, the third multi-port valve is preferably a four port distribution valve.

The guard separator 72, further separates the desired parent radionuclide from the daughter solution by capturing the parent radionuclide. Note that the guard separator 72 may have a plurality of sorbent materials such as ion exchange resins or uncharged carbonaceous materials.

The use of the separator 24, 61 and the guard separator 72 provide increased purity (i.e., impurity-free) of the desired daughter product. The use of both the separator 24, 61 and the guard separator 72 also permit a more compact system because a desired purity can be achieved with physically smaller separators.

Figure 4:
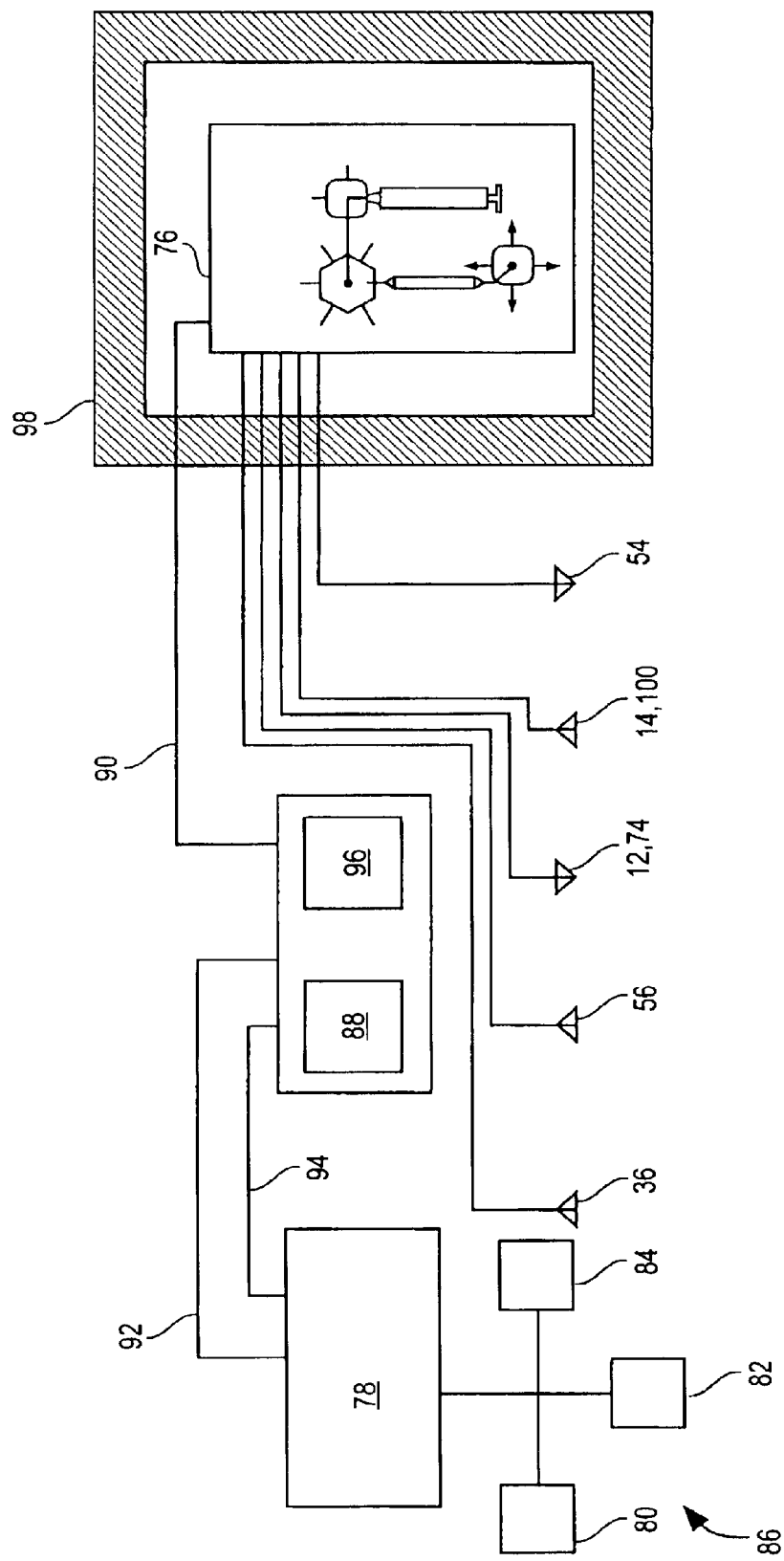
FIG. 4 illustrates one arrangement of the system that includes a processor operatively coupled to the pump, first, second, and third valves by way of an interface module and power supply, and also illustrates the pump, first, second, and third valves being housed in a protective radiation shielding.

Preferably, as shown in FIG. 4, a primary unit 76 including the pump 16, the first multi-port valve 18, the second multi-port valve 20, and the third multi-port valve 22, is in communication with a processor 78. The processor 78 is used to control the components of the primary unit 76 (pump 16, first multi-port valve 18, second multi-port valve 20, and third multi-port valve 22). Preferably, the processor 78 is a mini-processor 78, capable of executing instructions. The processor 78 can also be in communication with a memory 80, such as a memory chip, capable of storing data, or a hard drive. The processor 78 can also be in communication with an input device 82, such as a keyboard or a touch sensitive screen capable of entering data, and an output device 84, such as a display, graphical display, or a monitor for displaying the output of the processor. The processor-memory-input device-output device configuration can be, for example, a laptop computer 86.

Preferably, the primary unit 76 components (pump 16, first multi-port valve 18, second multi-port valve 20, and third multi-port valve 22) are coupled to an interface/power 88, 96 unit by, for example, a multi-conductor ribbon cable 90. The interface/power unit is preferably coupled to the processor 78 by way of cables 92, 94, such as a RS-232 serial communications cable 92 and TTL Digital Input/Output cable 94. The power unit 96 desirably provides a maximum of 24V of power. Those skilled in the art will readily appreciate the various control system configurations that can be used with the present separation systems 10, which control systems are within the scope and spirit of the present invention.

Preferably, as shown in FIG. 4, the primary unit components 16, 18, 20, 22 (FIG. 1) the growth vessel (not shown), and the temporary storage vessel (not shown) are enclosed by a radiation shielding 98 to reduce the radiation exposure to the operator and others (e.g., the patient), in accordance with ALARA principles. Such a configuration also assures that the primary unit components 16, 18, 20, 22, the growth vessel 60, and the temporary storage vessel 58 are not in contact with any high voltage sources. Rather, power is supplied by a power supply with a maximum output of 24 V DC, as necessary, to power the primary unit.

It should be noted that the radiation shielding 98 may be made from a variety of materials depending on the type of rays (alpha versus beta versus gamma rays) that will be produced, and thus depending on the particular application the first embodiment of the system 10 will be used for. For example, applications that produce extensive gamma rays may require lead shielding, while applications that produce alpha or beta rays may require Plexiglas™ shielding, and while other applications may not require any shielding.

The pump 16 includes a piston that reciprocates, moving in either in an upward or downward direction to drive the various materials and solutions throughout the system, as shown by the arrows shown beside the pump 16 in FIG. 2. The multi-port valves are actuated to direct the various solutions, such as the parent load solution 14, the daughter solution 12, the strip solution 56, and the wash solution 36 through the system 10.

Table 1 summarizes the valve positions and direction of pump movement for each step of a method that operates in a first reverse cow mode. The first reverse cow mode of operation includes 13 steps, 10 of which are repeated. The system is operated to carry out the steps pursuant to commands by the processor 78.

TABLE 1

| Step | Valve 1 (18) Positions | Valve 2 (20) Positions | Valve 3 (22) Positions | Direction of Pump |
|---|---|---|---|---|
| 1 | 3–4 (32,34) | 6 (52) | — | down |
| 2 | 3–4 (32,34) | 5 (50) | — | up |
| 4 | 3–4 (32,34) | 5 (50) | — | down |
| 5 | 3–4 (32,34) | 4 (48) | 1 (64) | up |
| 6 | 2–3 (30,32) | — | — | down |
| 7 | 3–4 (32,34) | 4 (48) | 1 (64) | up |
| 8 | 3–4 (32,34) | 2 (44) | — | down |
| 9 | 3–4 (32,34) | 4 (48) | 2 (66) | up |
| 10 | 3–4 (32,34) | 3 (46) | — | down |
| 11 | 3–4 (32,34) | 5 (50) | — | up |
| 12 | 2–3 (30,32) | — | — | down |
| 13 | 3–4 (32,34) | 4 (48) | 3 (70) | up |

The steps are as follows:

Step 1. The parent load solution 14 is loaded into the pump 16 (e.g., syringe). The first multi-port valve 18 provides flow communication between ports 3 and 4 (32, 34), the second multi-port valve 20 is in position 6 (52), and the syringe moves in a downward direction.

Step 2. The parent load solution 14 is transferred from the pump 16 to the growth vessel 60. At this point, the first multi-port valve 18 connects ports 3 and 4 (32, 34), the second multi-port valve 20 is in position 5 (50), and the pump 16 moves in an upward direction to drive the parent load solution 14 to the growth vessel 60.

Step 3. The parent load solution 14 is retained in the growth vessel 60 for a predetermined time during which the parent radionuclide decays to "grow" the desired daughter radionuclide. A combined parent-daughter solution thus results.

Step 4. The parent-daughter solution is transferred into the syringe 16. During transfer, the first multi-port valve 18 connects ports 3 and 4 (32, 34), the second multi-port valve 20 is in position 5 (50), and the pump 16 moves in a downward direction.

Step 5. The parent-daughter solution is transferred to the separator 24. The daughter radionuclide is retained by the separation medium (not shown) and the parent-daughter solution (with the daughter radionuclide separated therefrom) passes through the separator 24 and into the temporary storage vessel 58. To effect this transfer, the first multi-port valve 18 connects ports 3 and 4 (32, 34), the second multi-port valve 20 is in position 4 (48), the third multi-port valve 22 is in position 1 (64), and the pump 16 moves in an upward direction.

Step 6. The pump 16 is filled with wash solution 36. To carry out this step, the first multi-port valve 18 connects ports 2 and 3 (30, 32), and the syringe 16 moves in a downward direction.

Step 7. The separator 24 is washed with the wash solution 36. Any residual parent-daughter solution, as well as any retained parent radionuclide is washed from the separation medium and is directed to the temporary storage vessel 58. The temporary storage vessel 58 now includes a diluted parent load solution, which includes the parent-daughter solution (with the daughter radionuclide separated therefrom) from step 5, and the residual parent-daughter solution and a small amount of wash solution. To effect this step, the first multi-port valve 18 connects ports 3 and 4 (32, 34), the second multi-port valve 20 is in position 4 (48), the third multi-port valve 22 is in position 1 (64), and the pump 16 moves in an upward direction.

Note that in alternate methods, the residual parent-daughter solution can be washed and transferred to the waste vessel 54 by having the third multi-port valve 22 in position 3 (70). However, residual parent-daughter solution is not transferred to the waste vessel in the first cow mode to minimize loss of the remaining parent radionuclide.

Step 8. The pump 16 is filled with strip solution 56. In this step, the first multi-port valve 18 connects ports 3 and 4 (32, 34), the second multi-port valve 20 is in position 2 (44), and the pump 16 moves in a downward direction.

Step 9. The strip solution 56 is discharged through the separator 24. In stripping, the daughter radionuclide (retained by the separation medium) is stripped from the separation medium and is directed through the guard separator 72. The guard separator 72 captures any parent radionuclide carried by the daughter nuclide-laden stripping solution. A solution thus containing substantially impurity-free daughter radionuclide is discharged from the guard separator 72 into the product vessel 74. In this step, the first multi-port valve (18) connects ports 3 and 4 (32, 34), the second multi-port valve 20 is in position 4 (48), the third multi-port valve 22 is in position 2 (66), and the pump 16 moves in an upward direction.

Step 10. The pump 16 is filled with the diluted parent load solution from the temporary storage vessel 58. To effect this transfer, the first multi-port valve 18 connects ports 3 and 4 (32, 34), the second multi-port valve 20 is in position 3 (46), and the pump 16 moves in a downward direction.

Step 11. The solution is transferred to the growth vessel 60 for a predetermined time during which the parent radionuclide decays to "grow" the desired daughter radionuclide (as in step 3). Again, a combined parent-daughter solution results. For this step, the first multi-port valve 18 connects ports 3 and 4 (32, 34), the second multi-port valve 20 is in position 5 (50), and the pump 16 moves in an upward direction.

Step 12. The pump 16 is filled with wash solution 36. In this step, the first multi-port valve 18 connects ports 2 and 3 (30, 32), and the pump 16 moves in a downward direction.

Step 13. The wash solution 36 is discharged through the separator 24 and sent to waste. Thus, any waste solutions remaining in the separator 24 are washed away and are directed to the waste vessel 54. To effect this transfer, the first multi-port valve 18 connects ports 3 and 4 (32, 34), the second multi-port valve 20 is in position 4 (48), the third multi-port valve 22 is in position 3 (70), and the pump 16 moves in an upward direction.

Step 14. Steps 3 through 13 are repeated until a desired amount of the daughter radionuclide is separated and readied for use.

There are several contemplated variations to the above-described first reverse cow mode. For example, in this first mode, manual conditioning of the separator 24 prior to use of the automated system 10 is utilized. A variation of the first embodiment of the system can also provide for automatic conditioning of the separator 24. For example, the first multi-port valve 18 can be a three port distribution valve where, in FIG. 2, the first port 28 is in flow communication with a conditioning reagent solution, the second port 30 is in flow communication with a wash solution, the fourth port 34 is in flow communication with the uncoiled conduit or tube 38, which, in turn, is in flow communication with the second multi-port valve 20, and the third port 32 is in flow communication with the pump 16.

In carrying out conditioning, "pre-steps" 1 and 2 include: (1) filling the pump 16 with reagent (alternate first multi-port valve in position 1 (28), and the pump 16 moves in a downward direction); and, (2) transferring the reagent to the separator 24, for conditioning, and directing the reagent to waste (alternate first multi-port valve in position 4, second multi-port valve 20 in position 4 (48), third multi-port valve 22 in position 3 (68), and the pump 16 moves in an upward direction).

The illustrated system 10 incorporates several components, and the first reverse and conventional cow modes incorporate several steps, to reduce personnel exposure and to reduce the presence of radioactive materials outside the radioactive shield 98. For example, a container 100 storing the parent load solution 14 shown in FIG. 4 is located outside of the radiation shield 98. In that the parent load solution 14 is highly radioactive, it is beneficial to load the solution 14 into the primary unit 76—which is protected by the radiation shield 98—as soon as possible. Thus, the first step includes transferring all of the parent load solution 14 outside the radiation shield 98 to the growth vessel 60, which is inside the radiation shield 98. In such an arrangement, the daughter radionuclide is "grown" (that is, the parent decays) while the solution 14 is in the growth vessel 60, within the radiation shielding 98.

The parent load solution 14, 100 shown in FIG. 4 resides outside the shielding 98 because the parent load solution 14, 100 may arrive from a supplier in smaller separate shielding (not shown). Alternatively, the parent load solution 14, 100 can reside within the shielding 98. As discussed above, whether the parent load solution 14, 100 will reside in separate shielding (not shown) or whether it will reside within the shielding 98 typically depends on the application (i.e., the type of radiation that will be produced).

The product vessel 12, 74 can also reside inside or outside the shielding 98. If the product vessel 12, 74 resides inside the shielding 98, the shielding 272 may have to be opened every time the product is used, which could potentially expose the user to both product and parent radiation. If the product vessel 74 resides outside the shielding 98 (as shown in FIG. 4), it can reside in its own separate shielding (not shown), and the user would not have to open the shielding 98.

As discussed above shielding may not be required. Frequently, Plexiglas or glass faces to hoods will suffice for shielding of alpha and beta emitters.

Alternately still, the growth vessel 60 can be located within separate radiation shielding (not shown). In such an embodiment, a separate temporary storage vessel is not required, and a five-port distribution valve can be used. A method for operation of this alternate embodiment eliminates the first three steps of the first reverse cow mode (up through the daughter "growth" step), and begins with step four of the method described above.

As will be understood by those skilled in the art from a study of the present disclosure, the growth vessel 60 and temporary storage vessel 58 permit efficient use of the parent load solution 14. The temporary storage vessel 58 permits storage of a diluted parent load solution, which includes the parent load solution after the daughter radionuclide has been separated therefrom, mixed with wash solution and any residual parent load solution that is washed through the separator 24 with wash solution.

Both the temporary storage vessel 58 and the growth vessel 60 are required when the volume of diluted parent load solution (parent solution, residual parent load solution, and wash solution) exceeds the capacity of the pump 16. The diluted parent load solution volume can exceed the capacity of the pump when wash has been added to residual parent load solution. This typically arises after several iterations of the first reverse cow mode.

For example, in the first reverse cow mode, if the volume of diluted parent load solution (for example 6 mL) exceeds pump capacity (for example 5 mL), only 5 mL of diluted parent load solution is transferred to the separator, and thus 5 mL of diluted parent load solution with the daughter activity removed therefrom is transferred to the temporary storage vessel. One mL of diluted parent load solution remains in the growth vessel. Without the temporary storage vessel, the 5 mL of diluted parent load solution (with the daughter separated therefrom) would be remixed with the 1 mL of parent-daughter solution that remained in the growth vessel and could not be purified for use.

Figure 5:
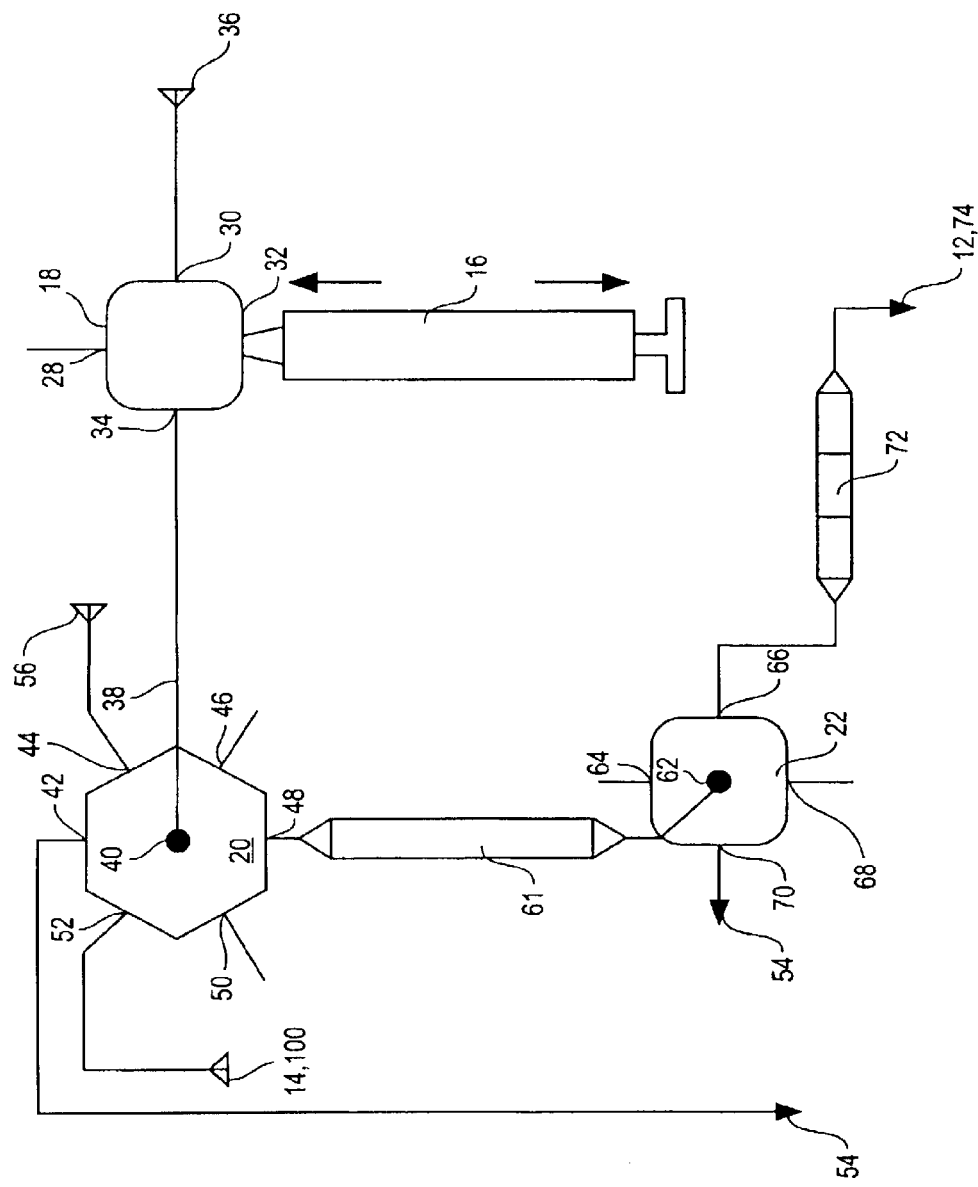
FIG. 5 is an illustration similar to FIG. 3 in which arrows are provided to indicate the direction of pump movement.

In a first conventional cow mode, the pump 16 piston moves either upward or downward to drive the various materials and solutions through the system, as shown by the arrows in FIG. 5. Table 2 summarizes the valve positions and direction of pump movement for each step of a first conventional cow mode procedure. The first conventional cow mode includes 8 steps, 5 of which are repeated. The system 10 carries out the steps pursuant to commands by the processor 78.

TABLE 2

| Steps | Valve 1 Position | Valve 2 Position | Valve 3 Position | Direction of Pump |
|---|---|---|---|---|
| 1 | 3–4 (32,34) | 6 (52) | — | down |
| 2 | 3–4 (32,34) | 4 (48) | 3 (70) | up |
| 3a | 2–3 (30,32) | — | — | down |
| 3b | 3–4 (32,34) | 4 (48) | 3 (70) | up |
| 5 | 2–3 (30,32) | — | — | down |
| 6 | 3–4 (32,34) | 1 (42) | — | up |
| 7 | 2–3 (30,32) | — | — | down |
| 8 | 3–4 (32,34) | 4 (48) | 2 (66) | up |

The steps are as follows:

Step 1. Fill the syringe 16 with parent load solution 14. To effect this transfer, the first multi-port valve 18 connects ports 3 and 4 (32, 34), the second multi-port valve 20 is in position 6 (52), and the pump 16 moves in the downward direction.

Step 2. Discharge the parent load solution 14 to the separator 61, and direct daughter radionuclide solution (with impurities accumulated during storage and shipping) to pass through to waste. Thus, parent radionuclide is captured by the separation medium (not shown) and the remainder of the solution (that can include contaminated daughter radionuclide), is directed to the waste vessel 54. This transfer is carried out with the first multi-port valve 18 connecting ports 3 and 4 (32, 34), the second multi-port valve 20 in position 4 (48), the third multi-port valve 22 in position 3 (70), and the pump 16 moving in the upward direction.

Step 3. The separator 61 is washed several times to remove impurities from the separation medium. This step has two sub-steps that can be repeated several times until the operator is satisfied that the separation medium is free from impurities. The two sub-steps are:

Step 3a. Fill the syringe 16 with wash solution. The first multi-port valve 18 connects 2 and 3 (30, 32), and the pump 16 moves in the downward direction.

Step 3b. Direct the wash solution 36 through the separator 61 to remove or rinse away any impurities. The wash solution 36 is directed to waste. To effect this transfer, the first multi-port valve 18 connects ports 3 and 4 (32, 34), the second multi-port valve 20 is in position 4 (48), the third multi-port valve 22 is in position 3 (70), and the pump 16 moves in the upward direction.

Step 4. The parent radionuclide 14 is retained in the separator 61 for a predetermined time during which the parent radionuclide decays to "grow" the desired daughter radionuclide. A combined parent-daughter solution thus results.

Step 5. The pump 16 is filled with wash solution to clean the pump 16. For this step, the first multi-port valve 18 connects ports 2 and 3 (30, 32), and the pump 16 moves in the downward direction.

Step 6. The wash solution 36 used to clean the pump 16 is discharged to waste. For this step, the first multi-port valve 18 connects ports position 3 and 4 (32, 34), the second multi-port valve 20 is in position 1 (42), and the pump 16 moves in the upward direction.

Step 7. The pump 16 is filled with wash solution that is used to wash the desired daughter radionuclide from the separator 61. To provide this transfer, the first multi-port valve 18 connects ports position 2 and 3 (30, 32), and the pump 16 moves in the downward direction.

Step 8. The wash solution 36 is discharged through the separator 61 and the guard separator 72 to the product vessel 74. The daughter radionuclide solution is washed from the separation medium through the guard separator 72. Any remaining parent radionuclide is captured on the guard separator 72, and a solution of substantially impurity-free daughter radionuclide is transferred from the guard separator 72 to the product vessel 74. To effect this transfer, the first multi-port valve 18 connects ports 3 and 4 (32, 34), the second multi-port valve 20 is in position 4 (48), the third multi-port valve 22 is in position 2 (66), and the pump 16 moves in the upward direction.

Step 9. Steps 7 through 8 can be repeated after waiting for the daughter radionuclide to grow in to a useful level. It should be noted that, during conventional cow mode, the strip solution 56, the growth vessel 60, and the temporary storage vessel 58 are not required. Thus, a three-port distribution valve can be used for the second multi-port valve. The common port 40 would be in flow communication with the uncoiled tube 38 (and thus the first multi-port valve), and the three side ports 42, 48, 52 would be in flow communication with the separator 61, parent load solution 14, and the waste vessel 54. However, because it is desired for the system 10 to operate in both forward and reverse cow modes, the system configuration described above is preferred.

It should also be noted that the system can incorporate various different separators 24, 61, guard separators 72, wash solutions 36, and strip solutions 56 depending on various factors, such the desired daughter radionuclide, the parent radionuclide and the mode of operation (e.g., forward or reverse cow mode).

A contemplated method and system can utilize one or more separation media. The separation medium or media utilized for a given separation is governed by the materials to be separated, as is well known. Preferred separation media are typically bead-shaped solid phase resins.

One preferred solid phase supported exchange resin is Bio-Rad® 50W-X8 resin in the $H^+$ form, which is commercially available from Bio-Rad Laboratories, Inc., of Richman, Calif. Other useful strong acid cation exchange media include the Dowex® 50W series of ion exchange resins and the Amberlite® IR series of ion exchange resins that are available from Sigma Chemical Co., St. Louis, Mo.

Anion exchange resins such as the Dowex® 1 series of anion exchange resins can also serve as separation media.

Another resin that can be used in the present process is a styrene-divinyl benzene polymer matrix and includes sulfonic, phosphonic, and gem diphosphonic acid functional groups chemically bonded thereto. Such a gem diphosphonic acid resin is commercially available from Eichrom Technologies, Inc., located at 8205 S. Cass Avenue, Darien, Ill. U.S.A, under the name Diphonix® brand resin. In the present process, the Diphonix® resin is used in the $H^+$ form. The characteristics and properties of Diphonix® resin are more fully described in U.S. Pat. Nos. 5,539,003, 5,449,462 and 5,281,631, whose disclosures are incorporated herein by reference.

The crown ethers that have been found to be particularly useful in increasing the uptake of radium and barium relative to calcium, in a liquid-solid phase system include 18-crown-6 (18C6), and 21-crown-7 (21 C7). The crown ethers are those crown ethers that have only a macrocyclic ring system.

Advantageously, such crown ethers, and in particular, the smaller crown ethers (e.g., 18C6) are relatively low cost reagents that provide a cost effective and procedurally efficient method for separating radium cations from water samples that contain calcium cations and that can also contain one or both of strontium and barium cations.

Another contemplated method utilizes two separation media that are extraction chromatographic and/or ion exchange resins. Such a two separation medium combination is particularly useful for separating actinium from thorium and other nuclides. A first exchange medium is a tetravalent actinide (TEVA®) resin, having a quaternary ammonium salt, specifically, a mixture of trioctyl and tridecyl methyl ammonium chlorides, sorbed on a water-insoluble support that is inert to the components of the exchange composition, as is discussed in E. P. Horwitz et al. *Analytica Chimica Acta* 310 (1995) 63–78, which is incorporated herein by reference.

The TEVA® resin is highly selective for ions having the tetravalent oxidation state, in the present process, Th-228 and Th-229 (whose valency are +4), relative to their decay products (whose valencies are +3 and lower such as actinium and radium). For example, the +4 valent thorium ions are bound to the TEVA® resin in nitric acid solution, whereas the actinium (Ac) and radium (Ra) ions (whose valencies are +3 and +2, respectively) are substantially unaffected by contact with the resin under the same conditions. The TEVA® resin is commercially available from Eichrom Technologies, Inc., located at 8205 S. Cass Avenue, Darien, Ill. U.S.A.

The combined aqueous Ra/Ac solution is then contacted with a second separation medium that is a second ion exchange medium, having a plurality of binding sites thereon adapted to bind ions having the next lower valency, which, here can be Ac-225 cations, to form an Ac-225-laden second ion exchange medium. The ion exchange medium (second exchange medium) serves to retain the Ac-225 (+3 valency) bound thereto and to pass through the radium isotopes (+2 valency) and any cations of +1 valency such as sodium, potassium ions or a proton, as well as anions and any non-actinium decay products of radium and decay products formed from the decay of actinium isotopes, such a francium-221 (+1 valency) and astatine-217 (−1 valency). The material thus remaining bound to the second ion exchange medium is essentially only Ac-225 because the binding sites thereon bind the +3 valent Ac-225 cations in preference to cations of lower valency and anions.

The Ac-225-laden ion exchange medium can be further rinsed with an acid solution such as an about 0.5 to about 10 M aqueous nitric or hydrochloric acid solution, preferably about 2.0 M to about 3.0 M nitric acid, to remove any residual cations of radium isotopes and cations of Ac-225 decay products from the chromatographic medium.

In a contemplated method, the second exchange medium (ion exchange medium) contains diphosphonic acid (DPA) ligands or groups. Several types of DPA-containing substituted diphosphonic acids are known in the art and can be used herein. An exemplary diphosphonic acid ligand has the formula

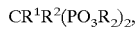
$CR^1R^2(PO_3R_2)_2,$ wherein R is selected from the group consisting of hydrogen (hydrido), a $C_1$–$C_8$ alkyl group, a cation, and mixtures thereof; $R^1$ is hydrogen or a $C_1$–$C_2$ alkyl group; and $R^2$ is hydrogen or a bond to a polymeric resin.

When $R^2$ is a bond to a polymeric resin, the phosphorus-containing groups are present at 1.0 to about 10 mmol/g dry weight of the copolymer and the mmol/g values are based on the polymer where $R^1$ is hydrogen. Exemplary exchange media containing diphosphonic acid ligands are discussed hereinbelow.

One such exchange medium is referred to as Dipex® resin, which is an extraction chromatographic material containing a liquid diphosphonic acid extractant belonging to a class of diesterified methanediphosphonic acids, such as di-2-ethylhexyl methanediphosphonic acid. The extractant is sorbed on a substrate that is inert to the mobile phase such as Amberchrome® CG-71 (available from TosoHaas, Montgomeryville, Pa.) or hydrophobic silica. In this extractant, $R^1$ and $R^2$ are H and one R is 2-ethylhexyl and the other is H.

Dipex® resin has been shown to have a high affinity for various tri-, tetra-, and hexa-valent actinides and lanthanides, such as cations of Ac-225, and to have a lower affinity for cations of radium and the decay products of Ac-225. This has been shown even in the presence of complexing anions such as fluoride, oxalate, and phosphate.

The active component of a preferred Dipex® resin is a liquid diphosphonic acid of the general formula,

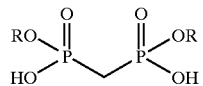

where R is $C_6$–$C_{18}$ alkyl or aryl, and preferably an ester derived from 2-ethyl-1-hexanol. A preferred compound is bis-2-ethylhexyl methanediphosphonic acid.

The active component DPA can be mixed with a lower boiling organic solvent such as methanol, ethanol, acetone, diethyl ether, methyl ethyl ketone, hexanes, or toluene and coated onto an inert support, such as glass beads, polypropylene beads, polyester beads or silica gel as known in the art for use in a chromatographic column. Acrylic and polyaromatic resins such as AMBERLITE®, commercially available from Rohm and Haas Company of Philadelphia, Pa., may also be used.

The properties and characteristics of Dipex® resin are more fully described in allowed U.S. patent application Ser. No. 08/467,402, filed Jun. 6, 1995, Horwitz et al. U.S. Pat. No. 5,651,883 the disclosure of which is incorporated herein by reference. Dipex® resin is available from Eichrom Technologies, Inc.

Another useful ion exchange resin is Diphosil® resin. Similar to the other DPA resins, Diphosil® resin contains a plurality of geminally substituted diphosphonic acid ligands such as those provided by vinylidene diphosphonic acid. The ligands are chemically bonded to an organic matrix that is grafted to silica particles. Diphosil® resin is available from Eichrom Technologies, Inc.

Yet another useful resin has pendent —$CR^1(PO_3R_2)_2$ groups added to a preformed water-insoluble copolymer by grafting; that is, the pendent phosphonate groups are added after copolymer particle formation. For these polymers, R is hydrogen (hydrido), a $C_1$–$C_8$ alkyl group, a cation or mixtures thereof, and $R^1$ is hydrogen or a $C_1$–$C_8$ alkyl group. A contemplated pendent —$CR^1(PO_3R_2)_2$ group for this group of resins has the formula shown below. The particles also contain zero to about 5 mmol/g dry weight of pendent aromatic sulfonate groups.

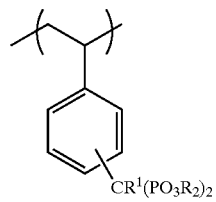

A contemplated pendent methylene diphosphonate as first formed typically contains two $C_1$–$C_8$ dialkyl phosphonate ester groups. Exemplary $C_1$–$C_8$ alkyl groups of those esters and other $C_1$–$C_8$ alkyl groups noted herein include methyl, ethyl, propyl, isopropyl, butyl, t-butyl, pentyl, cyclopentyl, hexyl, cyclohexyl, 4-methylcyclopentyl, heptyl, octyl, cyclooctyl, 3-ethylcyclohexyl and the like, as are well-known. An isopropyl group is a preferred R group. An $R^1$ $C_1$–$C_2$ alkyl group is a methyl or ethyl group, and $R^1$ is most preferably hydrogen.

After formation, the alkyl ester groups are hydrolyzed so that for use, R in the above formula is hydrogen (a proton), $Ca^{+2}$ ion or an alkali metal ion such as lithium, sodium, or potassium ions.

Preferably, the insoluble copolymer contains at least 2 mole percent reacted vinylbenzyl halide with that percentage more preferably being about 10 to about 95 mole percent. One or more reacted monoethylenically unsaturated monomers as discussed before are present at about 2 to about 85 mole percent, with this monomer preferably including at least 5 mole percent of an above monoethylenically unsaturated aromatic monomer such as styrene, ethyl styrene, vinyl toluene (methyl styrene) and vinyl xylene.

A useful insoluble copolymer also includes a reacted cross-linking agent (cross-linker). Reacted cross-linking agents useful herein are also quite varied. Exemplary useful cross-linking agents are selected from the group consisting of divinylbenzene, trimethylolpropane triacrylate or trimethacrylate, erythritol tetraacrylate or tetramethacrylate, 3,4-dihydroxy-1,5-hexadiene and 2,4-dimethyl-1,5-hexadiene. Divinylbenzene is particularly preferred here.

The amount of reacted cross-linker is that amount sufficient to achieve the desired insolubility. Typically, at least 0.3 mole percent-reacted cross-linker is present. The reacted cross-linking agent is preferably present at about 2 to about 20 mole percent.

These contemplated particles are the multi-step reaction product of a nucleophilic agent such as $CR^1(PO_3R_2)_2^-$, which can be obtained by known methods, with a substrate. Thus, $CHR^1(PO_3R_2)_2$, where R is preferably an alkyl group, is first reacted with sodium or potassium metal, sodium hydride or organolithium compounds, for example, butyllithium, or any agent capable of generating a diphosphonate carbanion. The resulting carbanion is then reacted with a substrate that is a before-discussed insoluble cross-linked copolymer of one or more of vinyl aliphatic, acrylic, or aromatic compounds and a polyvinyl aliphatic, acrylic, or aromatic compound, for example, divinylbenzene. That copolymer contains at least 2 mole percent of a reacted halogenated derivative of vinyl aromatic hydrocarbon such as vinylbenzyl chloride group, preferably from 10 to 95 mole percent, about 2 to about 85 mole percent of monovinyl aromatic hydrocarbon such as styrene and at least 0.3 mole percent of polyvinyl aliphatic and/or aromatic cross-linker such as divinylbenzene, preferably 2–20 mole percent.

The copolymer containing grafted methylene diphosphonate tetraalkyl ester groups in an amount corresponding to about 1.0 mmol/g of dry weight, preferably from 2 to 7 mmol/g of dry weight, is preferably reacted with a sulfonating agent such as chlorosulfonic acid, concentrated sulfuric acid or sulfur trioxide in order to introduce strongly acidic pendent aromatic sulfonic groups into their structure. The presence of the sulfonate pendent groups confers the additional advantage of hydrophilicity to the particles and leads to a surprising enhancement in the rate of cation complexation without adversely affecting the observed selectivity.

The reaction of the sulfonating agent with a grafted copolymer containing methylene diphosphonate groups is usually carried out when the recovered resin product in ester form is swollen by a halohydrocarbon such as dichloromethane, ethylene dichloride, chloroform, or 1,1,1-trichloroethane. The sulfonation reaction can be performed using 0.5 to 20.0 weight percent of chlorosulfonic acid in one of the mentioned halohydrocarbon solvents at temperatures ranging from about −25° to about 50° C., preferably at about 10° to about 30° C. The reaction is carried out by contacting resin preswollen for zero (unswollen) to about two hours with the above sulfonation solution for 0.25 to 20 hours, preferably 0.5 to two hours.

After completion of the sulfonation reaction, the particles are separated from the liquid reaction medium by filtration, centrifugation, decantation, or the like. This final, second resin product is carefully washed with dioxane, water, 1M NaOH, water, 1M HCl and water, and then dried.

The sulfonation reaction and work-up in water also hydrolyzes the phosphonate $C_1$–$C_8$ alkyl ester groups. Where sulfonation is not carried out, hydrolysis of the phosphonate esters can be carried out by reaction with an acid such as concentrated hydrochloric acid at reflux.

These contemplated particles contain as pendent functional groups both methylene diphosphonate and sulfonate groups, directly attached to carbon atoms of aromatic units or acrylate or methacrylate units in the polymer matrix. A contemplated resin displays high affinity towards a wide range of divalent, trivalent and multivalent cations over a wide range of pH values. At a pH value below one, the resins are able to switch from an ion-exchange mechanism of cation removal to a bifunctional ion-exchange/coordination mechanism due to the coordination ability of the phosphoryl oxygens. The sulfonic acid groups then act to make the matrix more hydrophilic for rapid metal ion access; the methylene diphosphonate groups are thus responsible for the high selectivity. Further details for the preparation of this resin can be found in Trochimczuk et al. U.S. Pat. No. 5,618,851, whose disclosures are incorporated by reference.

In a contemplated embodiment, the separator 24, 61 or guard separator 72 is loaded with "Sr Resin", an analytical resin available from Eichrom Technologies, Inc., that is described in U.S. Pat. No. 5,110,474, which disclosure is incorporated by reference. Briefly, the Sr Resin comprises an inert resin substrate upon which is dispersed a solution of the extractant, namely, a crown either dissolved in a liquid diluent.

The diluent is an organic compound that has (i) a high boiling point; that is, about 170° to 200° C., (ii) limited or no solubility in water, (iii) is capable of dissolving from about 0.5 to 6.0 M water, and (iv) is a material in which the crown ether is soluble. These diluents include alcohols, ketones, carboxylic acids and esters. Suitable alcohols include 1-octanol, which is most preferred, although 1-heptanol and 1-decanol are also satisfactory. The carboxylic acids include octanoic acid, which is preferred, in addition to heptanoic and hexanoic acids. Exemplary ketones include 2-hexanone and 4-methyl-2-pentanones, whereas esters include butyl acetate and amyl acetate.

The macrocyclic polyether can be any of the dicyclohexano crown ethers such as dicyclohexano-18-Crown-6, dicyclohexano 21-Crown-7, or dicyclohexano-24-Crown-8. The preferred crown ethers have the formula: 4,4'(5')[(R,R') dicyclohexano]-18-Crown-6, where R and R' are one or more members selected from the group consisting of H and straight chain or branched alkyls containing 1 to 12 carbons. Examples include, methyl, propyl, isobutyl, t-butyl, hexyl, and heptyl. The preferred ethers include dicyclohexano-18-crown-6 (DCH18C6) and bis-methylcyclohexano-18-crown-6 (DMeCH18C6). The most preferred ether is bis-4, 4'(5')-[(t-butyl)cyclohexano]-18-Crown-6 (Dt-BuCH18C6).

The amount of crown ether in the diluent can vary depending upon the particular form of the ether. For example, a concentration of about 0.1 to about 0.5 M of the most preferred t-butyl form (Dt-BuCH18C6) of the above-noted preferred crown ether in the diluent is satisfactory, with about 0.2 M being the most preferred. When the hydrogen form is used, the concentration can vary from about 0.25 to about 0.5 M. Concentrations above about 0.5 M of the crown ether in the diluent do not improve lead recovery when R and R' are H.

The preferred Sr Resin utilizes an inert resin substrate that is a non-ionic acrylic ester polymer bead resin such as Amberlite® XAD-7 (60 percent to 70 percent by weight) having a coating layer thereon of a crown ether such as 4,4'(5')di-t-butylcyclohexano-18-crown-6 (bis-t-butyl-cis-dicyclohexano-18-crown-6) (20 percent to 25 weight percent) dissolved in n-octanol (5 percent to 20 weight percent), having an extractant loading of 40 weight percent. E. P. Horwitz et al., *Solvent Extraction and Ion Exchange*, 10(2):313–16 (1992).

It has also been observed that Pb Resin, a related resin, also available from Eichrom Technologies, Inc. is also useful for purifying and accumulating Pb-212 for the production of Bi-212. Pb Resin has similar properties to Sr Resin except that a higher molecular weight alcohol; that is, isodecanol, is used in the manufacture of Pb Resin. E. P. Horwitz et al., *Analytica Chimica Acta*, 292, 263–73 (1994). It has been observed that Pb Resin permits subsequent removal of the Pb-212 from the resin, whereas it has been observed that Pb-212 becomes essentially irreversibly bound to the Sr Resin.

An improved Sr Resin also available from Eichrom Technologies, Inc. is even more selective. This separation medium is referred to as Super Pb(Sr) selective resin and comprises free-flowing particles having about 5 to about 50 weight percent of a di-4,4'(5')[$C_3$–$C_8$-alkylcyclohexano]18-Crown-6, such as di-t-butylcyclohexano-18-Crown-6, that exhibits a partition ratio between n-octanol and 1 M nitric acid ($D_{Crown}$=[Crown$_{Org}$]/[Crown]$_{Aq}$) of greater than about $10^3$ and usually of about $10^3$ to about $10^6$ dispersed onto an inert, porous support such as polymeric resin (e.g., Amberchrom® CG-71) or silica particles. The separation medium is free of a diluent, and particularly free of a diluent that is (i) insoluble or has limited (sparing) solubility in water and (ii) capable of dissolving a substantial quantity of water that is present in the Sr Resin.

In addition, the parent and desired daughter radionuclides also dictate the mode of operation. Specifically, if conventional cow mode is used, a separation medium that has an affinity for the parent radionuclide should be used. On the other hand, and if a reverse cow mode is used, a separation medium having a high affinity for the daughter radionuclide should be used. Other considerations, such as cost and availability of separation medium should also be taken into account.

The use and type of guard separator is also dictated by the parent and daughter radionuclides. For the reverse cow mode the guard separator is typically used to capture parent radionuclide and to allow the daughter radionuclide to flow through to the product vessel. In the conventional generator or forward cow mode, the guard separator again captures the parent radionuclide to afford an additional degree of purification of the desired daughter radionuclide.

Preferred wash and strip solutions that are used are also selected based upon the parent and daughter radionuclides and the desired use of the product. The reader is directed to Horwitz et al. U.S. Pat. No. 5,854,968 and Dietz et al. U.S. Pat. No. 5,863,439 for an illustrative discussion of separation medium and solutions.

Yet another separation medium is particularly useful for separating chaotropic anions in aqueous solution. This separation medium is available from Eichrom Technologies, Inc. under the designation ABEC®, and comprises particles having a plurality of covalently bonded —X—(CH$_2$CH$_2$-O)$_n$—CH$_2$CH$_2$R groups wherein X is O, S, NH or N—(CH$_2$CH$_2$O)$_m$—R$^3$ where m is a number having an average value of zero to about 225, n is a number having an average value of about 15 to about 225, R$^3$ is hydrogen, C$_1$–C$_2$ alkyl, 2-hydroxyethyl or CH$_2$CH$_2$R, and R is selected from the group consisting of —OH, C$_1$–C$_{10}$ hydrocarbyl ether having a molecular weight up to about one-tenth that of the —(CH$_2$CH$_2$O)$_n$— portion, carboxylate, sulfonate, phosphonate and —NR$^1$R$^2$ groups where each of R$^1$ and R$^2$ is independently hydrogen, C$_2$–C$_3$ hydroxyalkyl or C$_1$–C$_6$ alkyl, or —NR$^1$R$^2$ together form a 5- or 6-membered cyclic amine having zero or one oxygen atom or zero or one additional nitrogen atom in the ring. The separation particles have a percent CH$_2$O/mm$^2$ of particle surface area of greater than about 8000 and less than about 1,000,000. Exemplary chaotropic anions include simple anions such as Br$^{-1}$ and I$^{-1}$ and radicals such as TcO$_4^{-1}$, ReO$_4^{-1}$ or IO$_3^{-1}$. The chaotropic anion can also be a complex of a metal cation and halide or pseudohalide anions. Mixtures of anionic dyes can also be separated using the ABEC® separation medium. A particularly useful separation that can be effected using this separation medium is that of $^{99m}$TcO$_4^{-1}$ (pertechnetate-99m) from an aqueous solution that also contains parental $^{99}$MoO$_4^{-2}$ (molybdate-99) ions. Further details concerning the ABEC® separation medium and its uses can be found in U.S. Pat. Nos. 5,603,834, 5,707,525 and 5,888,397.

The present system and method are configured to operate substantially free from air or gas, thereby permitting greater flexibility in the use of bead-supported separation media. Specifically, air or gas travelling through such separation medium can cause channeling in which less than desired intimate contact between the solution and the separation medium can occur. As such, the present system is configured as a liquid transport and process system. One advantage to such an air- or gas-less system is that there is no air or gas that must be processed or filtered (due to possible radioactive contaminant entrainment). As such the present system can be of a less complicated design than those that use combinations of air and liquid.

In such a bead-supported separation medium system, the support beads that comprise the separation medium are packed into the column. When a solution is passed through the beads, the solution can flow over, through and around the beads, coming into intimate contact with the separation medium. If air or gas is introduced into the column, the air or gas can push aside the beads, causing a "channel" through the beads. This can result in the solution passing through the channel without flowing over or around the beads; rather, the solution passes through the channel without contacting the separation medium. This can result in less efficient purification of the desired radionuclide.

Thus, the present system, which does not require the use of air or gas to separate some of the solutions from one another, provides other advantages over those systems that use such a non-liquid stream (i.e., air or gas) separation method. Thus, the present system advantageously provides flexibility in that different types of separation media can be used.

The sizes and dimensions of the tubing and type of valves used vary depending on the desired flow rates. In one study, it was found that 10–50 mL/min flow rates sufficed for transferring liquids through the tubing (not through the separators), and 20–25 mL/min were found to be the optimal flow rates. When pumping liquids through the separator (a beaded column separator was used in the study), flow rates of 100–500 μL/min sufficed, and 500 μL/min was found to be the optimal flow rate. In general, the maximum flow rate is 1 second for the entire syringe volume. The minimum flow rate is 0.0005 times the pump (syringe) volume per pulse of the linear actuator where the pulse occurs in less than a millisecond.

In one embodiment, Hamilton 'Modular Valve Positioner' with digital communications valves was used. For example, the model 4-5 MVP Plug valve with 4-port distribution, and the model 6-5 MVP Plug valve with 6 port distribution was used.

Fittings can be made from a variety of materials. One such material is commercially available from the 3M Company under the trademark KEL-F®. Another material from which the fittings can be made is chlorotrifluoroethylene (CTFE). The fittings are HPLC fittings, commercially available from Hamilton Company.

One acceptable material for the tubing is polytetrafluoroethylene (PTFE), commercially available under the trademark TEFLON®. Tubing that is used are standard commercial grades and sizes. For example, tubing commercially available having a 0.042 inch or 0.028 inch inner diameter can be used. As will be recognized by those skilled in the art, the size of the tubing should correspond to the sizes of the fittings, equipment, and vessels used. In the study, fittings commercially available from the above-noted Hamilton Company were used. These fittings have an outside diameter of 0.074 inches. These fittings are preferred in that they permit use of larger (inner) diameter tubing, which is preferred because such tubing reduces backpressure on the system, and thus permits greater flow rates. Smaller inner diameter tubing can also be used, however, at reduced flow rates.

Figure 7:
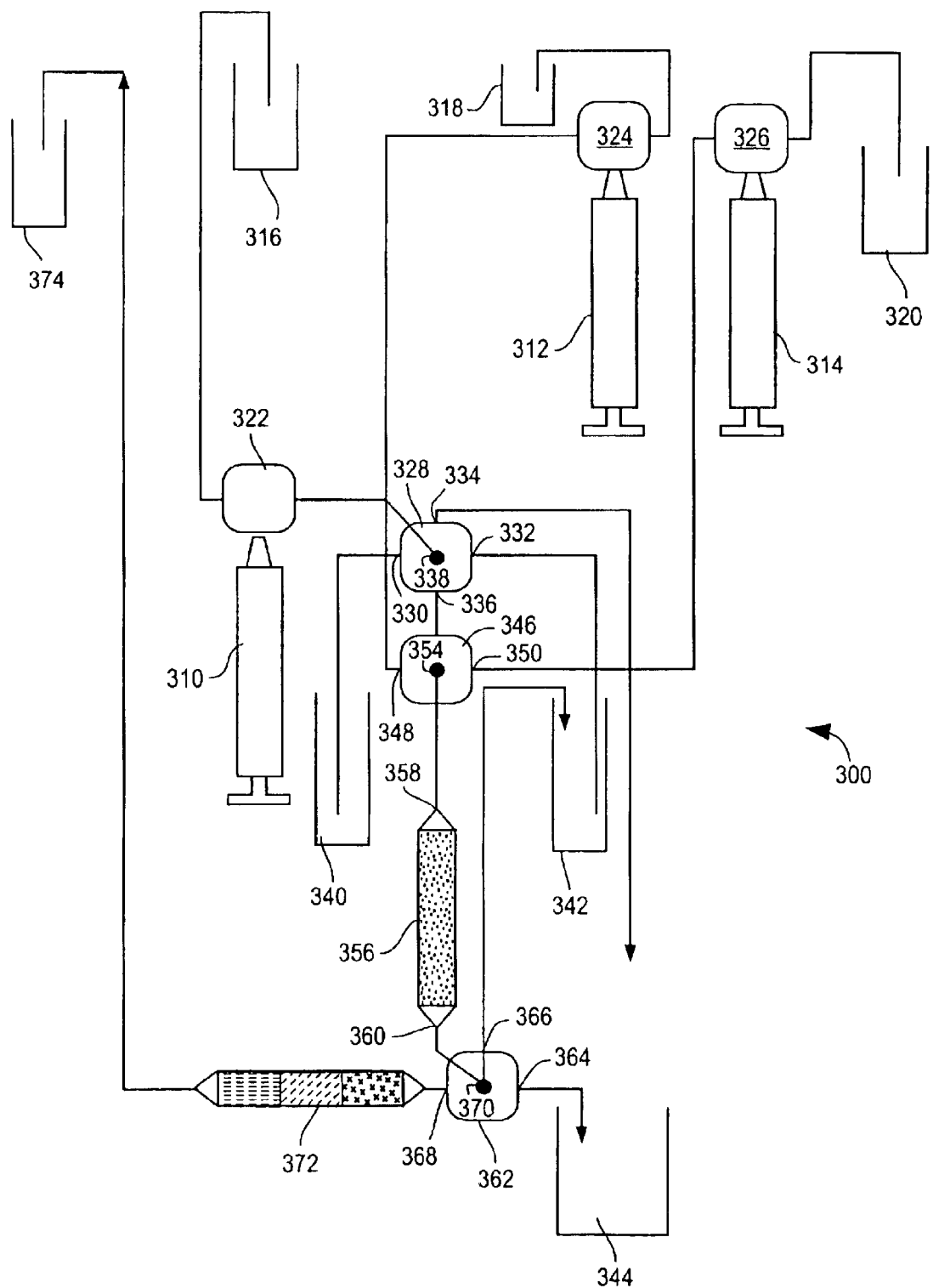
FIG. 7 is a partial schematic view of yet another embodiment of the automated radionuclide separation system that includes three pumps and six multi-port valves.
Figure 8:
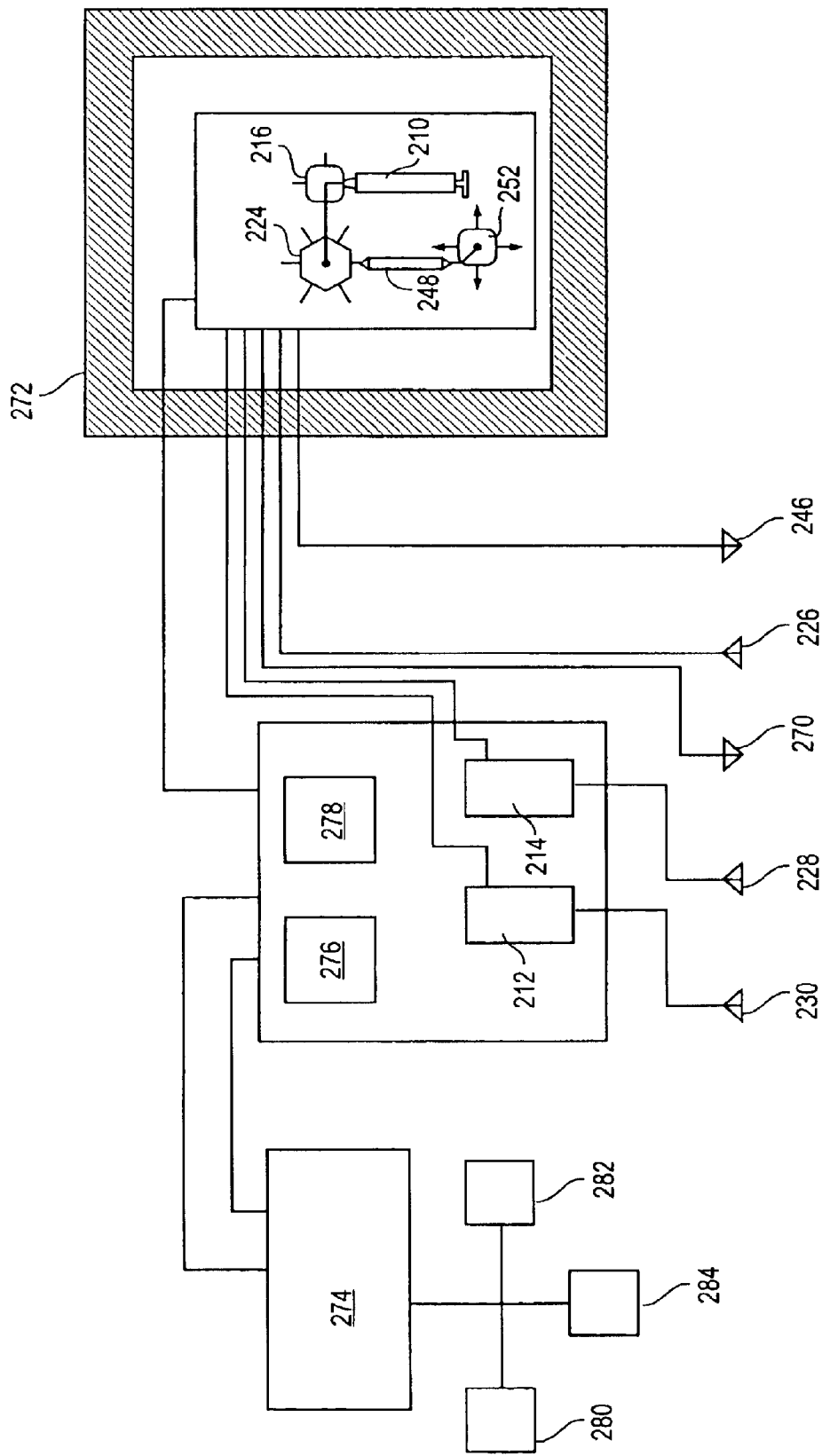
FIG. 8 illustrates the embodiment of the system of FIG. 6 in which a processor is operably coupled to the pumps and valves by way of an interface module and power supply, and in which a first pump, and first, fourth, and fifth valves are housed in a protective radiation shielding.
Figure 9:
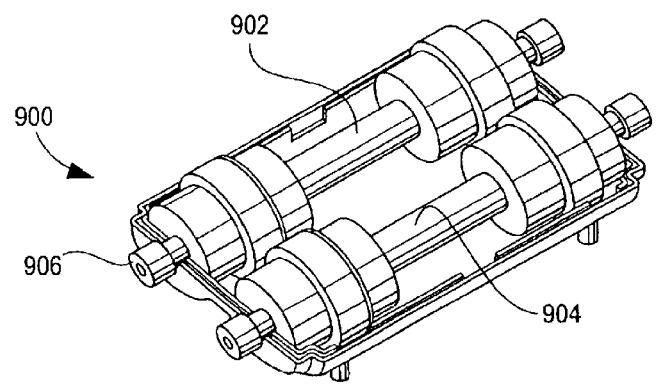
FIG. 9 is a perspective cut away view of a modular unit having a separator and a guard column unit for use with the present system.

Other embodiments of the system are illustrated in FIGS. 7–9. Of course, other operating methods correspond to these embodiments. However, all of these embodiments and operating methods are common in that they are gas-free or air-free and operate in either forward or reverse cow modes.

Figure 6:
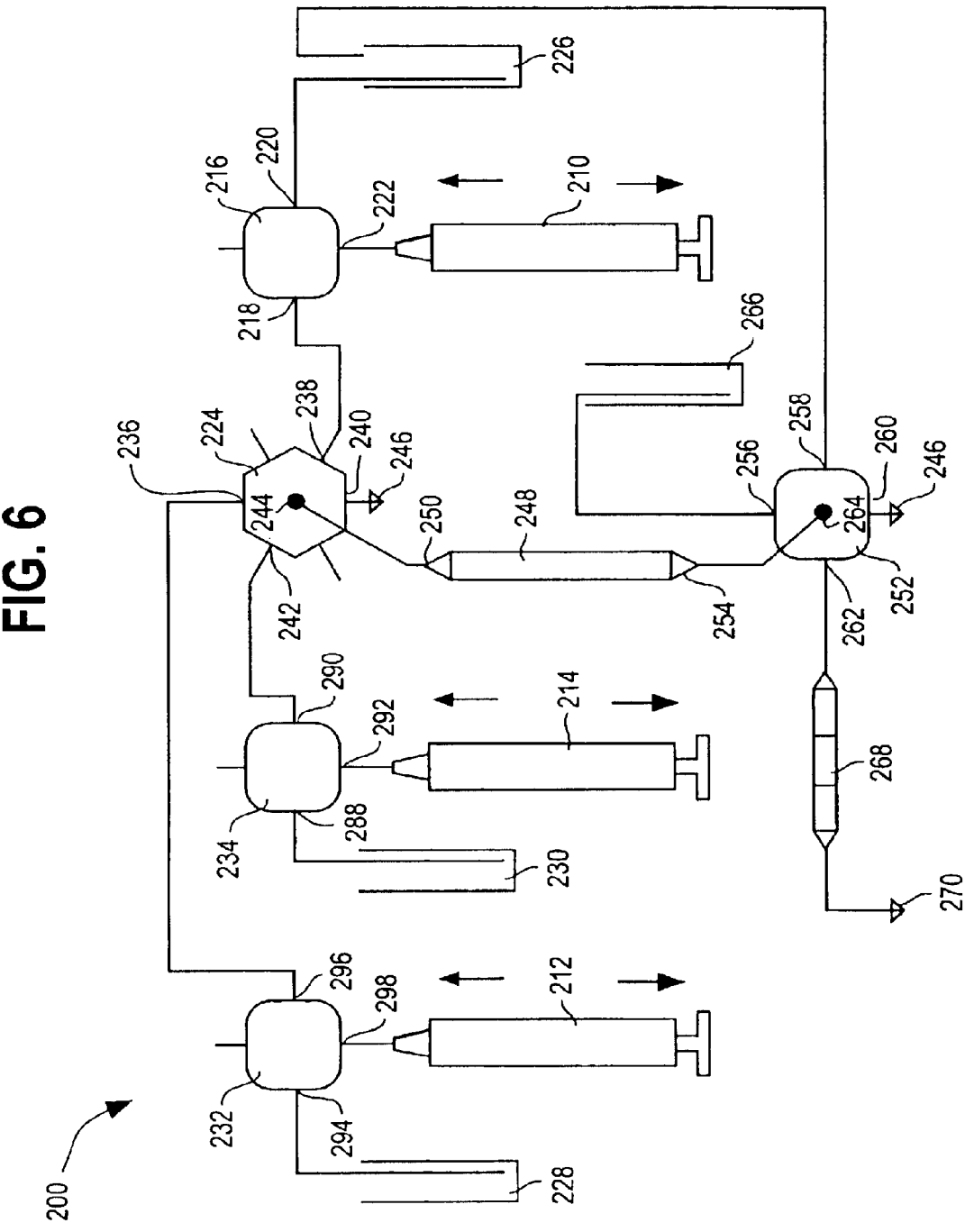
FIG. 6 is a partial schematic illustration of another embodiment of the automated radionuclide separation system that includes three pumps and five multi-port valves, and further illustrates, by way of indicating arrows, the direction of pump movement.

An alternate embodiment of the system 200 that includes three syringes 210, 212, 214 is shown in FIG. 6. This embodiment uses three pumps 210, 212, 214 to reduce contamination of wash and strip solutions with parent load solutions.

This embodiment 200 includes a first multi-port valve 216 having at least three ports 218, 220, 222 in flow communication with a fourth multi-port valve 224, a parent load solution 226 (which can be stored in a vessel), and a first pump 210. The alternate system also includes second and third pumps 212, 214 in flow communication with strip 228 and wash solutions 230 by way of second and third multi-port valves 232, 234. The second and third pumps 212, 214 are also in flow communication with the fourth multi-port valve 224. The second and third valves 232, 234 can be, for example, three or four port selection valves.

The fourth multi-port valve 224 can include four side ports 236, 238, 240, 242 and one common port 244. The side ports 236, 238, 240, 242 are in flow communication with a waste vessel 246, and the first, second and third pumps 210, 212, 214 by way of the first, second, and third valves 216, 232, 234. The common port 244 is in flow communication with a separator 248.

The separator 248 is in flow communication with the fourth multi-port valve 224 at a first end 250, and in flow communication with a fifth multi-port 252 valve at a second end 254. The fifth multi-port valve 252 has four-side ports 256, 258, 260, 262 and one common port 264. The side ports 256, 258, 260, 262 are in flow communication with a parent wash collection vessel 266, the waste vessel 246, the parent load solution 226, and a guard separator 268. As with the earlier described embodiment, the guard separator 268 is in flow communication with a product vessel 270.

It should be noted that in this embodiment, a user manually transfers the contents of the parent wash collection vessel 266 to the parent load solution vessel 226. This is done to recycle residual parent radionuclide that is directed to the parent wash collection vessel 266 during separation procedures. The user can also concentrate the residual parent radionuclide solution by removing wash solution from the parent wash collection vessel before transferring the contents to the parent load solution vessel.

Still another embodiment 300, similar to that shown in FIG. 6, is illustrated in FIG. 7. This embodiment 300 includes first, second and third pumps 310, 312, 314 in flow communication with a parent load solution 316, a wash solution 318, and a strip solution 320, respectively, by way of, first, second and third valves 322, 324, 326. The first, second and third valves 322, 324, 326 preferably have three ports, and can be, for example, two port distribution valves having a common port and two side ports. Alternately, three or four port selection valves can be used.

The first pump 310 is in flow communication with a fourth multi-port valve 328 having four side ports 330, 332, 334, 336 and a common port 338. The side ports 330, 332, 334, 336 are in flow communication with a growth vessel 340, a temporary storage vessel 342, a waste vessel 344 and a fifth multi-port valve 346. The common port 338 is in flow communication with the first pump 310.

The fifth multi-port valve 346 has three-side ports 348, 350, 352 and one common port 354. The three side ports 348, 350, 352 are in flow communication with the second and third pumps 312, 314, and the fourth multi-port valve 328. The common port 354 is in flow communication with a first end 358 of a separator 356.

A second end 360 of the separator 356 is in flow communication with a sixth multi-port valve 362 having three side ports 364, 366, 368 and a common port 370. The three side ports 364, 366, 368 are in flow communication with the waste vessel 344, the temporary storage vessel 342, and a guard separator 372, which is in flow communication with a product vessel 374.

The embodiment 300 of FIG. 7 allows for automatic recycling of residual parent radionuclide solution mixed with wash solution by use of the growth vessel 340 and temporary storage vessel 342. The steps of recycling the residual parent radionuclide are similar to the steps described above in the first reverse cow mode.

FIG. 8 illustrates a variation of the embodiment 200 of FIG. 6, that includes radiation-shielding 272. The first pump 210, the separator 248, and the first, fourth and fifth valves 216, 224, 252 can be enclosed by the radiation shielding 272.

The parent load solution 226 shown in FIG. 8 resides outside the shielding 272 because the parent load solution 226 may arrive in smaller separate shielding (not shown). Alternatively, the parent load solution 226 can reside within the shielding 272. As discussed above, whether the parent load solution 226 will reside in separate shielding (not shown) or whether it will reside within the shielding 272 typically depends on the application (i.e., the type of radiation that will be produced).

The product vessel 270 can also reside inside or outside the shielding 272. If the product vessel 270 resides inside the shielding 272, the shielding 272 may have to be opened every time the product 272 is used, which could potentially expose the user to both product and parent radiation. If the product vessel 270 resides outside the shielding 272 (as shown in FIG. 8), it can reside in its own separate shielding (not shown), and the user would not have to open the shielding 272.

As discussed above shielding may not be required. Frequently, plexiglass or glass faces to hoods will suffice for shielding of alpha and beta emitters.

The valves 216, 224, 232, 234, 252 and pumps 210, 212, 214 (FIG. 6) of this embodiment are also controlled by a processor 274 through an interface module 276 and power supply 278, as shown in FIG. 8, similar to the configuration shown in FIG. 4. The interface module 276 and power supply 278 are, in turn, coupled to the processor 274. A control system can include a processor 274, a memory 280, an input device 282, and an output device 284, such as a graphical display.

As will be recognized by those skilled in the art, many variations of the present systems, including both the one pump and three pump embodiments 10, 200, 300 are possible and are within the scope and spirit of the present invention. The methods of using the various embodiments are similar to those described above as first reverse cow and conventional cow modes.

For example, one method of operating the embodiment of FIG. 6 in reverse cow mode is noted in the steps below. Again, arrows in FIG. 6 show the direction of the piston of each pump.

Step 1. Fill the first pump 210 with parent load solution 226. To effect this transfer, the first valve 216 connects ports 2 and 3 (220, 222), and the first pump 210 moves in a downward direction.

Step 2. Discharge the parent load solution 226 to the separator 248. The desired daughter radionuclide is held by the separation medium and the solution containing parent radionuclide and impurities (contaminants) passes through the separator 248. The solution containing parent radionuclide and impurities is directed to the parent load solution vessel 226. To effect this transfer, the first valve 216 connects ports 1 and 3 (218, 222), the fourth valve 224 is in the second position 238, the fifth valve 252 is in the second position 258, and the first pump moves 210 in an upward direction.

Step 3. Fill the third pump 214 with wash solution 230. In this step, the third valve 234 connects ports 1 and 3 (288, 292) of the third valve, and the third pump 214 moves in the downward direction.

Step 4. Discharge the wash solution through the separator 248 to wash any residual parent radionuclide from the separation medium. The residual parent radionuclide and wash solution are directed to the parent wash collection vessel 266. To effect this transfer, the third valve 234 connects ports 2 and 3 (290, 292) of the third valve, the fourth valve 224 is in the fourth position 242, the fifth valve 252 is in the first position 256, and the third pump 214 moves in the upward direction.

Step 5. Fill the second pump 212 with strip solution 228. In this step, the second valve 232 connects ports 1 and 3 (294, 298) of the second valve, and the second pump 212 moves in the downward direction.

Step 6. Discharge the strip solution through the separator 248 to strip the captured daughter radionuclide, and to direct the daughter radionuclide to the guard separator 268. The daughter radionuclide passes through the guard separator 268, in which the guard separator 268 captures any residual parent radionuclide. The solution of substantially impurity-free daughter radionuclide is then directed to the product vessel 270. To carry out this transfer, the second valve 232 connects ports 2 and 3 (296, 298), the fourth valve 224 is in the first position 236, the fifth valve 252 is in the fourth position 262, and the second pump 212 moves in the upward direction.

Step 7. Fill the third pump 214 with wash solution 230. In this step, the third valve 234 connects ports 1 and 3 (288, 292), and the third pump 214 moves in the downward direction.

Step 8. Discharge the wash solution onto the separator 248 to wash any strip solution from the separator and tubing. In this step, any residual parent radionuclide and the wash solution are directed to waste vessel 246. This step is carried out with the third valve 234 connecting ports 2 and 3 (290, 292), the fourth valve 224 in the fourth position 242, the fifth valve 252 in the third position 260, and the third pump 214 moving in the upward direction.

Step 9. Wait a predetermined time for decay of the parent radionuclide to produce the desired daughter radionuclide while the parent load solution is in the parent load solution vessel 226.

Step 10. Repeat steps 1 through 9.

Chemical purity is vital to a safe and efficient medical procedure because the radionuclide is generally conjugated to a biolocalization agent prior to use. In order to minimize the adverse effects of radiolytic degradation on the chemical and radionuclidic purity of the product, the separation columns may be used a single time so that radiolytic degradation products do not accumulate and interfere with subsequent purification procedures. In one embodiment depicted in FIG. 9 the separation and guard columns 902, 904 are contained in a modular unit 900. The modular unit 900 has connectors 906 on either end of the separator and guard columns.

Figure 10:
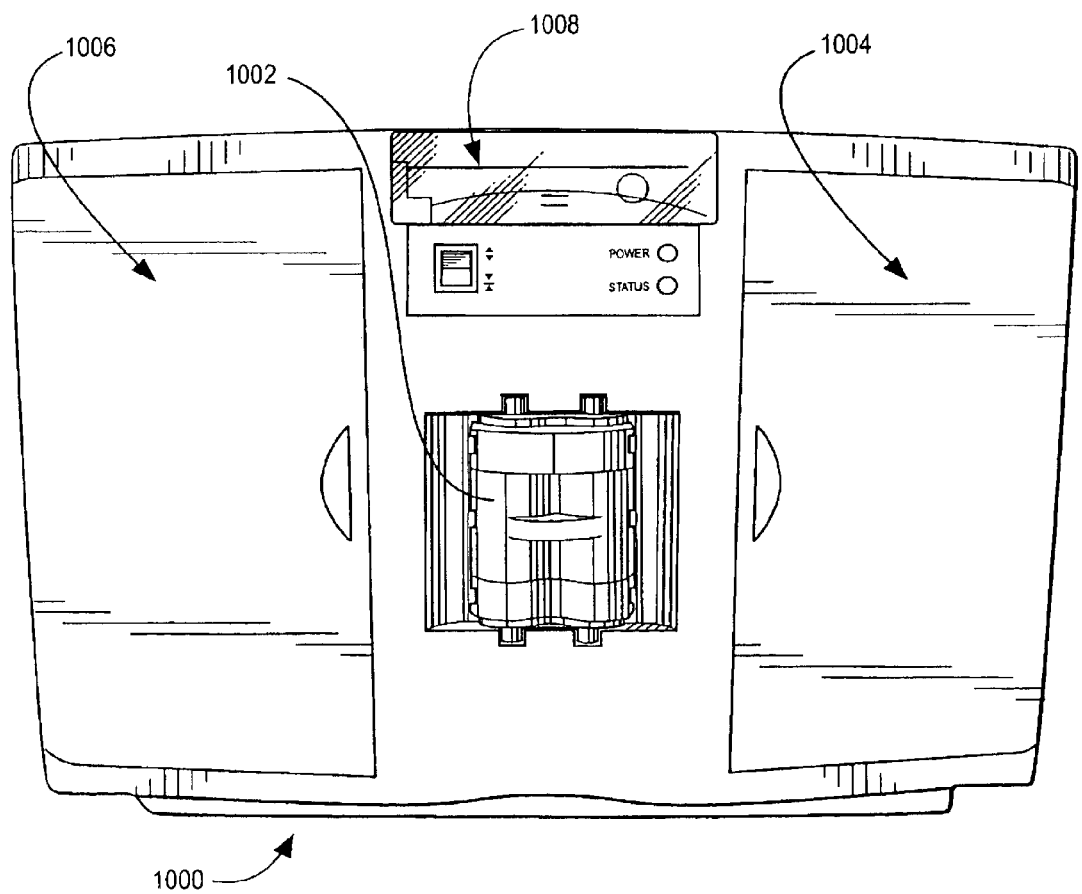
FIG. 10 is a front view of a housing for the system with the modular separator and guard column unit inserted therein.

FIG. 10 depicts a housing 1000 for the present system in which the modular unit 1002 containing the separator and guard column is removably connected. This permits easy interchangeability of the modular unit 1002 for one time use of the separator columns. The compartment 1008 in this embodiment is used to house a removable connectable product vessel, and the compartments 1004 and 1006 may hold, for example, the parent load solution, the strip solution, the growth vessel and/or the storage vessel, and waste.

Figure 11:
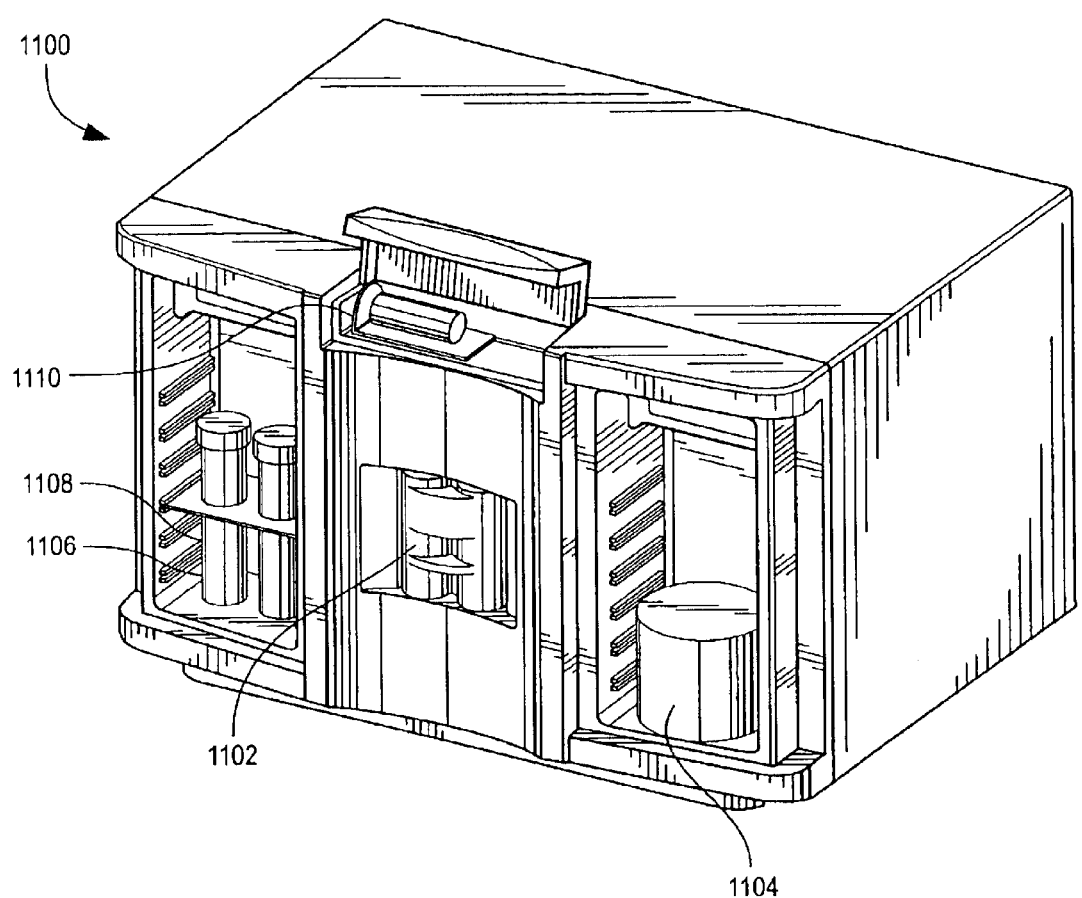
FIG. 11 is a perspective view of the system housing illustrating the removable containers for various solutions for the system.

FIG. 11 shows the housing 110 having contained therein a vessel 1104 containing a radioactive parent source solution, a vessel 1106 containing a wash solution, and a vessel 1108 containing a strip solution. Also depicted is the product vessel 1110, and the separator module 1102. Each of these may be disconnected and easily removed from the housing 1100. This especially allows for single use of the separator module 1102, although if desired the separator module may be retained in the housing 1100 for multiple uses thereof.

Figure 12:
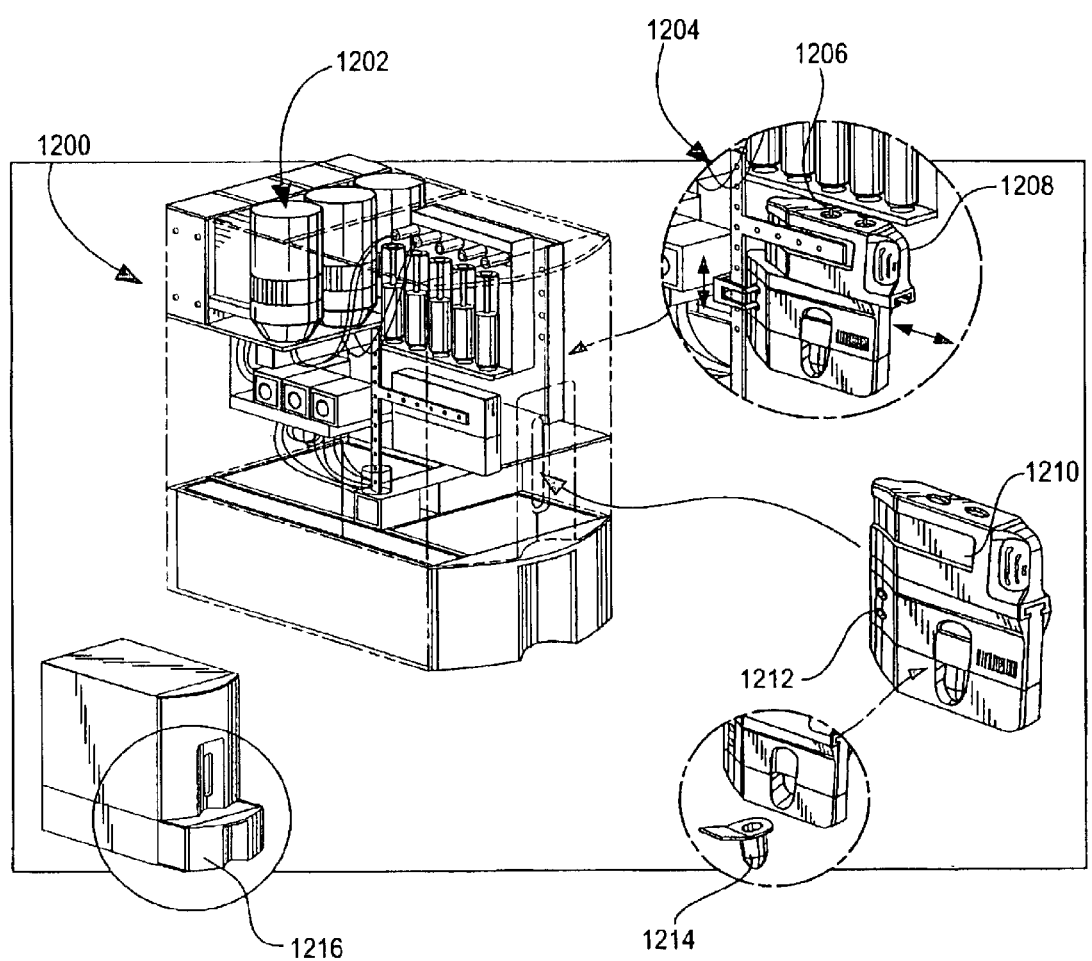
FIG. 12 is a perspective depiction of an alternate embodiment of the system.

An alternative embodiment of the system is depicted in FIG. 12. In this embodiment, a main unit 1200 has removable vessels 1202 that may contain a wash solution, a parent solution, a strip solution, etc. As depicted by unit 1204, a modular unit 1208 connects the system via connectors 1206. Various types of connectors may be used to connect the modular unit 1208. The modular unit 1208 in this embodiment slideably engages the main unit 1200 using guide 1210 and positioning pinholes 1212. The modular unit 1208 also has a pull-down tab 1214 for removing the desired daughter radionuclide. A pull out catch tray 1216 is also provided as shown in FIG. 12.

Figure 13:
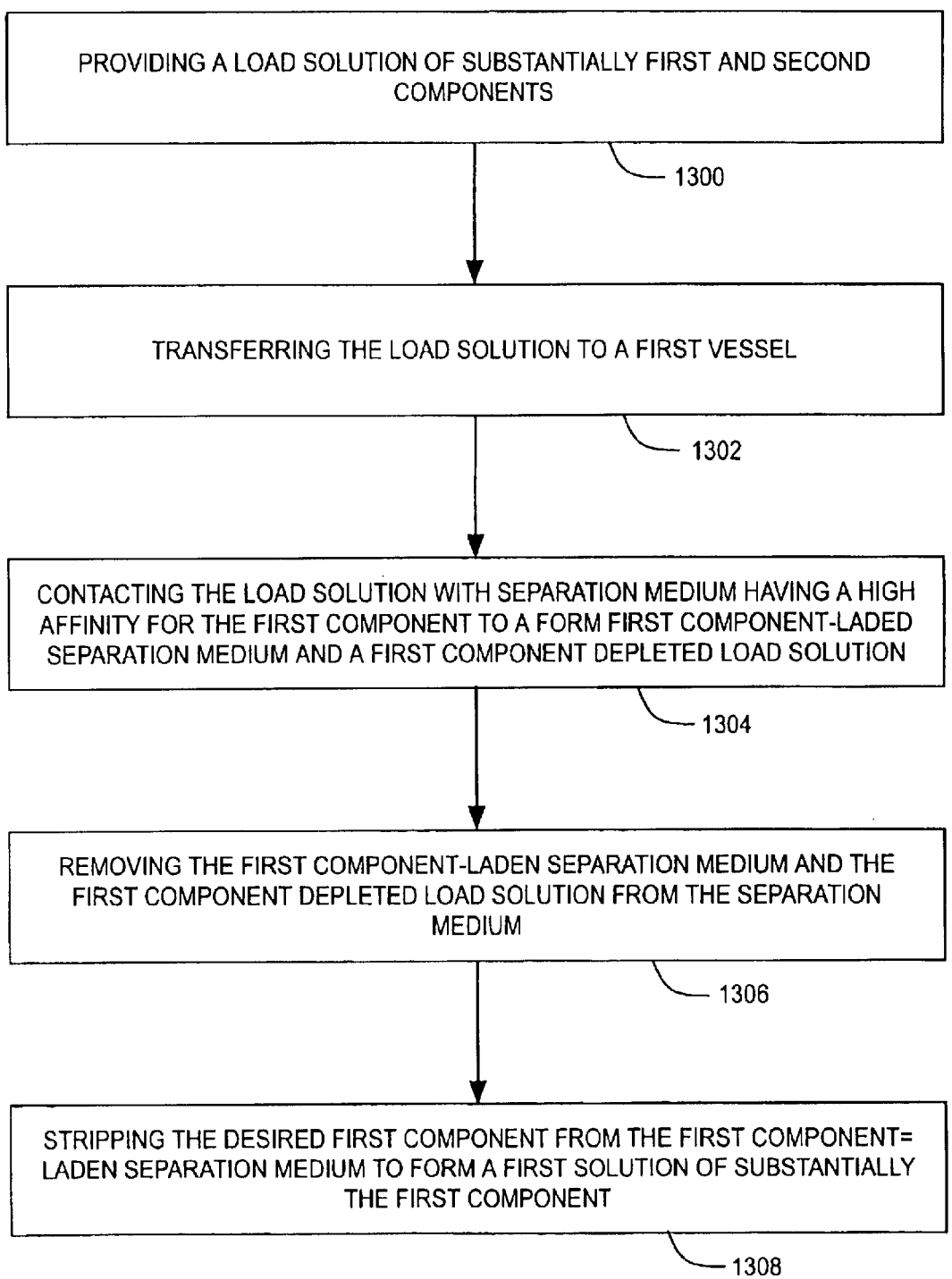
FIG. 13 is a flow diagram depicting the method for separating a first solution of substantially a first component from an associated load solution of substantially first and second components.

One embodiment of a method for separating a first component from an associated load solution of substantially first and second components is depicted in FIG. 13. A load solution of substantially first and second components is provided in a first step 1300. The load solution is then transferred to a first vessel in step 1302. The load solution is contacted with separation medium having a high affinity for the first component to a form first component-laden separation medium and a first component depleted load solution in step 1304. The first component depleted separation medium and a first component-depleted load solution is removed from the separation medium in step 1306. The desired first component is then stripped from the first component-laden separation medium to form a first solution of substantially the first component in step 1308.

The method may also be implemented in software, or combinations of hardware and software. For example, the method depicted in FIG. 13 may be contained in a computer readable medium containing embedded computer program code segments for separating a first component from an associated load solution of substantially first and second components. The computer program code segments may be:

a first computer program code segment that transfers the load solution to a first vessel;

a second computer program code segment that contacts the load solution with separation medium having a high affinity for the first component to a form first component-laden separation medium and a first component depleted load solution;

a third computer program code segment that removes the first component-laden separation medium and the first component depleted load solution from the separation medium; and a fourth computer program code segment that strips the desired first component from the first component-laden separation medium to form a first solution of substantially the first component.

Figure 14:
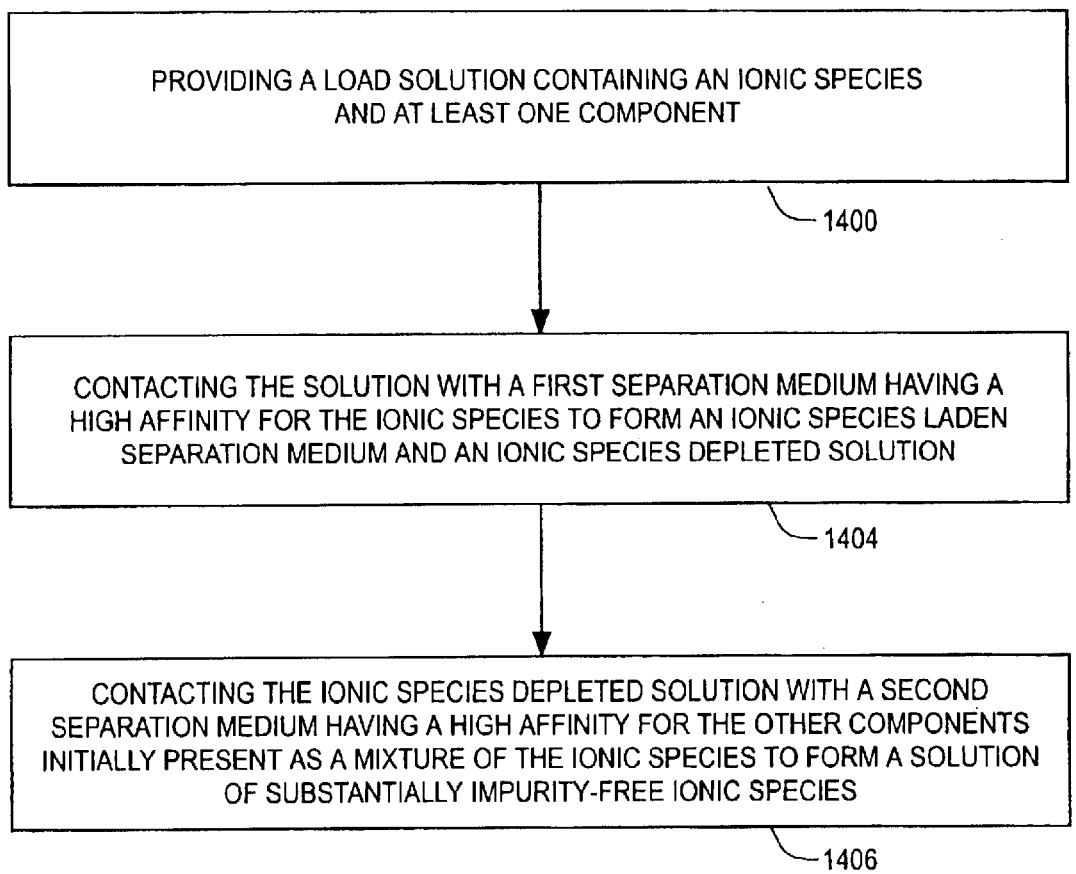
FIG. 14 is a flow diagram depicting the method for separating an ionic species from a load solution containing the ionic species and at least one component to form an end solution of substantially impurity-free ionic species.

Another embodiment of a method for separating an ionic species from a load solution containing the ionic species and at least one component to form an end solution of substantially impurity-free ionic species is depicted in FIG. 14. In a first step 1400 a load solution containing the ionic species and at least one component is provided. The solution is contacted in step 1404 with a first separation medium having a high affinity for the ionic species to form an ionic species laden separation medium and an ionic species depleted solution. The ionic species depleted solution is contacted with a second separation medium having a high affinity for the other components initially present as a mixture of the ionic species to form a solution of substantially impurity-free ionic species in step 1406.

This method may also be implemented in software, or combinations of hardware and software. For example, the method depicted in FIG. 14 may be contained in a computer readable medium containing embedded computer program code segments for separating an ionic species from a load solution containing the ionic species and at least one component to form an end solution of substantially impurity-free ionic species. The computer program code segments may be:

a first computer program code segment that transfers a solution containing at least one component to a radioactive in-growth vessel;

a second computer program code segment that contacts the solution with a first separation medium having a high affinity for the ionic species to form an ionic species laden separation medium and a daughter laden solution; and a third computer program code segment that contacts the daughter laden solution with a second separation medium having a high affinity for the parent radionuclide to form a solution of substantially impurity-free daughter radionuclide.

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

EXAMPLE 1

Separation of Barium(Ba) from a Mixture with Lead(Pb), Thorium(Th) and Uranium(U)

The generation of bismuth-212 ($^{212}Bi$) for radiotherapeutic purposes can be achieved by "milking" or eluting $^{212}Bi$ from a Pb-selective chromatographic column containing purified $^{212}Pb$ (10.6 hour half-life). Because of the short half-life of $^{212}Pb$, it must be obtained on a daily basis from its longer-lived parents, usually 3.6 day $^{224}Ra$. The objective of the following study was to illustrate the feasibility of selectively separating $^{212}Pb$ from a mixture of $^{232}U$, $^{228}Th$, and $^{224}Ra$. Naturally occurring $^{238}U$, $^{232}Th$, Ba, and Pb were used as stand-ins for the $^{212}Pb$ parents. Super Pb(Sr)-selective resin available from Eichrom Technologies, Inc. was utilized in a before-described automated radionuclide separation unit to demonstrate the separation.

A 0.29 mL bed volume column containing Super Pb(Sr) resin was placed in a separation unit. The conditions and results of the separation are shown in the following table:

| Column Bed Volume | 0.29 mL (cross sectional area of 0.125 cm²) | | | |
| Flow Rate | 0.2 mL/minute or 1.6 mL/cm²/minute | | | |
| Resin | 20–50 µm particle size | | | |

| Fraction Collected | Volume (mL) | Ba | Pb | Th | U |
|---|---|---|---|---|---|
| Eluate from 3 M HNO₃ load | 10 | 60 | 0 | 185 | 191 |
| 0.5 M HNO₃ wash | 10 | 41 | 0 | 7 | 11 |
| H₂O strip | 2.0 | 0.8 | 0 | 0 | 0 |
| 0.05 M NH₄ Citrate Strip | 1.0 | 0 | 156 | 0 | 0 |
| 0.05 M NH₄ Citrate Strip | 1.0 | 0 | 6 | 0 | 0 |
| 0.05 M NH₄ Citrate Strip | 1.0 | 0 | 0 | 0 | 0 |
| Total Collected | | 102 | 162 | 192 | 202 |

| | | µg | | | |
|---|---|---|---|---|---|
| | Volume | Ba | Pb | Th | U |
| Feed Solution | 10 mL | 101 | 162 | 191 | 202 |

The data show that Ba, Th, and U are not retained to any significant extent by the Pb-selective resin. On the other hand, Pb is strongly retained in 0.5 M HNO₃, but readily stripped with dilute ammonium citrate. No detectable Ba, Th, or U was found in the Pb fraction indicating a decontamination factor of greater than $10^3$. The mass balance, i.e., the amount added compared to the quantity recovered for each constituent, is quantitative within experimental error.

EXAMPLE 2

Separation of Thorium from Uranium Using TEVA Resin

The separation of thorium (Th) from uranium (U) is important in the production of bismuth-212 ($^{212}Bi$) generators. The long-lived parent isotopes of $^{212}Bi$ are $^{228}Th$ (1.9 year half-life) and $^{232}U$ (70 year half-life). A 50 milliCurie $^{212}Bi$ generator system requires 2.34 mg of $^{232}U$ but only 6.09 µg of $^{228}Th$. By removing Th from U, a smaller, more efficient $^{212}Bi$ generator system can be developed because a much smaller chromatographic column is required to retain $^{228}Th$ than $^{232}U$.

A very efficient separation of Th from U can be obtained using TEVA resin that is available from Eichrom Technologies, Inc. Thorium is strongly retained from solutions of 1 to 6 M HNO₃, whereas U is poorly retained and largely elutes from the TEVA resin column during loading and rinsing.

The separation of $^{228}Th$ from $^{232}U$ was simulated using $^{232}Th$ and $^{238}U$, the most stable naturally occurring isotopes of these elements. The separation was carried out using a separation system substantially as shown in FIG. 2. A 150 μL bed volume column was utilized. The conditions and result of the separation are shown in the following table:

| Column Bed Volume | 0.158 mL (2 cm × 0.518 cm i.d.) | | |
|---|---|---|---|
| Flow Rate | 0.2 mL.minute or 1.6 mL/cm²/min | | |
| TEVA Resin | 50–100 μm | | |

| | Volume Collected | μg | |
|---|---|---|---|
| Fraction Collected | (mL) | Th | U |
| Eluate from 2 M HNO₃ load | 2 | 0 | 2137 |
| Wash 2.0 M HNO₃ | 0.5 | 0 | 655 |
| Wash 2.0 M HNO₃ | 0.5 | 0 | 226 |
| Wash 2.0 M HNO₃ | 0.5 | 0 | 58 |
| Wash 2.0 M HNO₃ | 0.5 | 0 | 16 |
| Wash 2.0 M HNO₃ | 2.0 | 0 | 0 |
| Strip 1.0 M HCl | 2.0 | 202 | 0 |
| Total Collected | | 202 | 3092 |

| | | μg | |
|---|---|---|---|
| Feed Solution | Volume (mL) | Th | U |
| 2.0 M HNO₃ | 2.0 | 200 | 3000 |

No U was detectable in the Th fraction and no Th was detectable in the uranium fraction. Decontamination factors of U from Th and Th from U are $10^4$ and $10^3$ respectively. The mass balance; that is, the amount added to the quantity recovered for each constituent, is quantitative within experimental error.

EXAMPLE 3

Separation of $^{207}$Bi from $^{133}$Ba and i. $^{139}$Ce(III) Using Dipex Resin The generation of bismuth-213 ($^{213}$Bi) for radiotherapeutic purposes can be achieved by "milking" or eluting $^{213}$Bi from a chromatographic column that strongly retains actinium-225 ($^{225}$Ac; 10 day half-life). The $^{225}$Ac can contain radium-225 ($^{225}$Ra), therefore, rejection of Ra on loading the chromatographic column is important. The recovery of $^{213}$Bi from the column is achieved by eluting with an acid having a soft donor anion, such as HCl.

The objective of the following study was to demonstrate the separation of $^{207}$Bi (stand-in for $^{213}$Bi) from barium-133 ($^{133}$Ba is a stand-in for $^{225}$Ra) and cerium-139 ($^{139}$Ce is a stand-in for $^{225}$Ac) using a separation system substantially as shown in FIG. 2. Dipex® extraction chromatographic resin was chosen as the chromatographic resin to achieve the necessary selectivity (see U.S. Pat. No. 5,854,968). Dipex® extraction chromatographic resin is available from Eichrom Technologies, Inc.

A 0.16 mL bed volume column was slurry packed with 20–50 μm Dipex® Resin. A mixture of 7×10⁴ cpm $^{133}$Ba, 2×10⁵ cpm $^{139}$Ce, and 3×10⁴ cpm $^{207}$Bi in 2.0 mL of 1.0 M HNO₃ was loaded onto the column. As expected, $^{133}$Ba broke through immediately and showed no significant retention. After loading, the column was rinsed with 1.0 M HNO₃ to further remove $^{133}$Ba activity. Over 95% of the $^{139}$Ce was retained by the Dipex® column. The remaining 5% of the $^{139}$Ce followed $^{133}$Ba, and was removed by rinsing.

Bismuth-207 was also strongly retained by the Dipex® column when loaded in 1.0 M HNO₃, but was readily removed from the column using 2.0 M HCl. Cerium-139, on the other hand, is strongly retained by Dipex® resin in hydrochloric acid and was not eluted under these conditions. Using the automated system, more than 93% of $^{207}$Bi was recovered with a reduction in $^{133}$Ba and $^{139}$Ce concentrations by a factor of $10^3$ to $10^4$.

Each of the patents, applications and articles cited herein is incorporated by reference. The use of the article "a" or "an" is intended to include one or more. Further, the terms "in flow communication with", "in communication with", "coupled", and "operatively coupled" are intended to not only include two components directly linked to one another, but also are intended to include two components indirectly linked to one another by way of, for example, other intermediate components, cable and/or tubing, located between the components.

From the foregoing it will be observed that numerous modifications and variations can be effectuated without departing from the true spirit and scope of the novel concepts of the invention. It is to be understood that no limitation with respect to the specific embodiment illustrated is intended or should be inferred. The disclosure is intended to cover by the appended claims all such modifications as fall within the scope of the claims.

What is claimed is:

1. A gas-free system for separating substantially impurity-free radioactive daughter product from an associated radioactive parent load solution, the system comprising:
   a pump;
   a first multi-port valve having at least two ports, a first port of the first multi-port valve being in flow communication with the pump;
   a second multi-port valve including at least four ports, a first port of the second multi-port valve being in flow communication with the associated parent load solution, a second port of the second multi-port valve being in flow communication with an associated strip solution, and a third port of the second multi-port valve being in flow communication with the first multi-port valve, and a fourth port;
   a separator being in flow communication with the fourth port of the second multi-port valve;
   a third multi-port valve including at least two ports, a first port of the third multi-port valve being in flow communication with the separator opposite the fourth port of the second multi-port valve, and a second port of die third multi-port valve being in flow communication with an associated product vessel;
   a conduit extending between a third port of the second multi-port valve and the first multi-port valve; and
   a processor operatively coupled to the pump, first multi-port valve, the second multi-port valve, and the third multi-port valve.

2. The system in accordance with claim 1, wherein the separator and the product vessel form modular units that are detachably connected to the second and third multi-port valves.

3. The system in accordance with claim 1, wherein the first, second and third flow valves form a valve system, and wherein each of the parent load solution, the strip solution, the separator, and the product vessel are detachably connected to the valve system.

4. The system in accordance with claim 1 including a guard column, wherein the third multi-port valve is in flow communication with the associated product vessel by the guard column, and wherein the separator, the guard column and the product vessel form modular units that are detachably connected to the second and third multi-port valves.

29

5. The system in accordance with claim 1 further comprising an associated radioactive in-growth vessel in flow communication with the second multi-port valve, and an associated temporary storage vessel in flow communication with the second multi-port valve, the second multi-port valve including six ports.

6. The system in accordance with claim 5, wherein the first, second and third flow valves form a valve system, and wherein each of the parent load solution, the strip solution, the separator, the product vessel, the growth vessel and the storage vessel are detachably connected to the valve system.

7. The system in accordance with claim 1 including a radiation shield enclosing the pump, the separator, guard column, and the first, second, and third valves.

8. The system in accordance with claim 1 including a wash solution in flow communication with the first or second multi-port valve, the first multi-port valve including three ports.

9. A system for separating desired daughter radionuclides from an associated parent load solution, the system comprising:
- a first pump;
- a first multi-port valve including at least three ports, the first valve in flow communication with the first pump, and with the associated parent load solution;
- a second pump;
- a second multi-port valve including at least three ports, the second valve in flow communication with the second pump, and with an associated strip solution;
- a third pump;
- a third multi-port valve including at least three ports, the third pump in flow communication with the third valve, and with an associated wash solution;
- a fourth multi-port valve including at least four ports, the fourth valve in flow communication with the first, second and third valves;
- a separator in flow communication with the fourth valve;
- a fifth multi-port valve including at least three ports, the fifth multi-port valve in flow communication with the separator, and an associated product vessel; and,
- a processor operatively coupled to the first, second third, fourth and fifth valves, and to the first, second and third pumps.

10. The system in accordance with claim 9 including a guard column, wherein the fifth valve is in flow communication with the product vessel by way of the guard column.

11. The system in accordance with claim 10, wherein the first, second, third, fourth and fifth flow valves form a valve system, and wherein each of the parent load solution, the strip solution, the separator, the guard column, the product vessel, the growth vessel and the storage vessel are detachably connected to the valve system.

12. The system in accordance with claim 9 wherein the system is substantially free from gas.

13. The system in accordance with claim 10 including a radiation shield, wherein the first, fourth and fifth valves, the first pump, the separator and the guard column are enclosed by a radiation shield.

14. A system for separating a first solution of substantially a first component from an associated load solution of substantially first and second components, the system comprising:
- a pump;
- a first multi-port valve having at least two ports, a first port of the first multi-port valve being in flow communication with the pump;

30

- a second multi-port valve including at least four ports, a first port of the second multi-port valve being in flow communication with the associated load solution, a second port of the second multi-port valve being in flow communication with an associated strip solution, and a third port of the second multi-port valve being in flow communication with the first multi-port valve, and a fourth port;
- a separator being in flow communication with the fourth port of the second multi-port valve; and
- a third multi-port valve including at least two ports, a first port of the third multi-port valve being in flow communication with the separator opposite the fourth port of the second multi-port valve, and a second port of the third multi-port valve being in flow communication with an associated product vessel that contains the separated first solution of the first component.

15. The system in accordance with claim 14 including a guard column, wherein the third multi-port valve is in flow communication with the associated product vessel by way of the guard column.

16. The system in accordance with claim 15, wherein the separator, the guard column, and the product vessel form modular units that are detachably connected to the second and third multi-port valves.

17. The system in accordance with claim 15, wherein the first, second and third flow valves form a valve system, and wherein each of the load solution, the strip solution, the separator, the guard column, and the product vessel are detachably connected to the valve system.

18. The system in accordance with claim 14 including a computer processor operatively coupled to the pump, the first multi-port valve, the second multi-port valve, and the third multi-port valve.

19. The system in accordance with claim 14 further comprising an associated radioactive in-growth vessel in flow communication with the second multi-port valve, and an associated temporary storage vessel in flow communication with the second multi-port valve, the second multi-port valve including six ports.

20. The system in accordance with claim 19, wherein the first, second and third flow valves form a valve system, and wherein each of the parent load solution, the strip solution, the separator, the product vessel, the growth vessel and the storage vessel are detachably connected to the valve system.

21. The system in accordance with claim 14 including a wash solution in flow communication with the first multi-port valve, the first multi-port valve including three ports.

22. The system in accordance with claim 21, wherein the first, second and third flow valves form a valve system, and wherein each of the parent load solution, the strip solution, the separator, the product vessel, and the wash solution are detachably connected to the valve system.

23. The system in accordance with claim 14, wherein at least one of the first and second components is radioactive.

24. The system in accordance with claim 14, wherein at least one of the first and second components is an ionic species.

25. The system in accordance with claim 14, wherein at least one of the first and second components is an ionic analyte.

26. The system in accordance with claim 14 wherein the system is substantially free from gas.

27. A system for separating a first ionic species from a load solution having the first ionic species and at least one component, the system comprising:
- a first pump;

a first multi-port valve including at least three ports, the first valve in flow communication with the first pump, and with the load solution;

a second pump;

a second multi-port valve including at least three ports, the second valve in flow communication with the second pump, and with an associated strip solution;

a third pump;

a third multi-port valve including at least three ports, the third valve in flow communication with the third valve, and with an associated wash solution;

a fourth multi-port valve including at least four ports, the fourth valve in flow communication with the first, second and third valves;

a separator in flow communication with the fourth valve;

a fifth multi-port valve including at least three ports, the Fifth multi-port valve in flow communication with the separator, the associated solution, and an associated product vessel that contains the first ionic species; and, a processor operatively coupled to the first, second, third, fourth and fifth valves, and to the first, second and third pumps.

28. The system in accordance with claim 27 including a guard column, wherein the fifth valve is in flow communication with the product vessel by way of the guard column.

29. The system in accordance with claim 28, wherein the first, second, third, fourth and fifth flow valves form a valve system, and wherein each of the parent load solution, the strip solution, the separator, the guard column, the product vessel, the growth vessel and the storage vessel are detachably connected to the valve system.

30. The system in accordance with claim 27 wherein the system is substantially free from gas.

31. The system in accordance with claim 27 wherein at least one of the first ionic species and the component is radioactive.

* * * * *